(12) United States Patent
Skora et al.

(10) Patent No.: US 8,776,800 B2
(45) Date of Patent: Jul. 15, 2014

(54) STERILE DRAPE HAVING MULTIPLE DRAPE INTERFACE MECHANISMS

(75) Inventors: Brooke Skora, San Diego, CA (US); Jose Jacquez, Spring Valley, CA (US); How-Lun Chen, San Diego, CA (US)

(73) Assignee: Carefusion 2200, Inc., San Diego, CA (US)

( * ) Notice: Subject to any disclaimer, the term of this patent is extended or adjusted under 35 U.S.C. 154(b) by 538 days.

(21) Appl. No.: 12/895,235

(22) Filed: Sep. 30, 2010

(65) Prior Publication Data
US 2012/0080040 A1    Apr. 5, 2012

(51) Int. Cl.
*A61B 19/08*    (2006.01)
*A61B 17/00*    (2006.01)

(52) U.S. Cl.
USPC ............................... 128/853; 128/849; 606/1

(58) Field of Classification Search
USPC ........... 128/851, 852; 600/1, 101, 121; 606/1, 606/130; 901/49–50
See application file for complete search history.

(56) References Cited

U.S. PATENT DOCUMENTS

| | | | |
|---|---|---|---|
| 594,692 | A | 11/1897 | Henneberg |
| 3,923,166 | A | 12/1975 | Fletcher |
| 4,414,962 | A | 11/1983 | Carson |
| 4,750,475 | A | 6/1988 | Yoshihashi |
| 5,201,908 | A | 4/1993 | Jones |
| 5,361,583 | A | 11/1994 | Huitema |
| 5,441,042 | A | 8/1995 | Putman |
| 5,624,398 | A | 4/1997 | Smith et al. |
| 5,762,458 | A | 6/1998 | Wang et al. |
| 5,792,135 | A | 8/1998 | Madhani et al. |
| 5,807,240 | A | 9/1998 | Muller et al. |
| 5,807,377 | A | 9/1998 | Madhani et al. |
| 5,808,665 | A | 9/1998 | Green |
| 5,855,583 | A | 1/1999 | Wang et al. |
| 5,890,781 | A * | 4/1999 | Ryder ................. 312/1 |
| 5,976,122 | A | 11/1999 | Madhani et al. |
| 6,096,004 | A | 8/2000 | Meglan et al. |
| 6,149,252 | A * | 11/2000 | Browning ............ 312/1 |
| 6,301,526 | B1 | 10/2001 | Kim et al. |

(Continued)

FOREIGN PATENT DOCUMENTS

WO    WO-9740759    11/1997

OTHER PUBLICATIONS

ISA/KR, International Search Report and Written Opinion for International Application No. PCT/US2011/049229, 11 pages, Mar. 22, 2012.

*Primary Examiner* — Patricia Bianco
*Assistant Examiner* — Camtu Nguyen
(74) *Attorney, Agent, or Firm* — Arent Fox LLP

(57) ABSTRACT

A sterile drape configured for isolating a portion of a surgical device within a sterile environment, comprising: a plurality of drape interface mechanisms comprising: at least one drape/handle interface mechanism comprising a first ring defining a first opening through the sterile drape and configured for coupling with a control mechanism, the control mechanism comprising a surgical device for controlling a surgical instrument; and at least one drape/shaft interface mechanism comprising a second ring defining a second opening through the sterile drape, and configured for sealingly receiving a shaft there through as the shaft moves with a piston and is detachably coupled with the piston, wherein the piston is configured for responding to a first set of control signals sent by a first mechanical manipulation mechanism via a first connector by moving between a proximal end and a distal end of a first mechanical slave cylinder.

12 Claims, 51 Drawing Sheets

(56) References Cited

U.S. PATENT DOCUMENTS

| | | |
|---|---|---|
| 6,364,888 B1 | 4/2002 | Niemeyer et al. |
| 6,607,475 B2 | 8/2003 | Doyle et al. |
| 7,331,967 B2 | 2/2008 | Lee et al. |
| 7,470,268 B2 | 12/2008 | Doyle et al. |
| 7,865,266 B2 | 1/2011 | Moll et al. |
| 8,105,319 B2 | 1/2012 | Doyle et al. |
| 2002/0128633 A1 | 9/2002 | Brock et al. |
| 2004/0049205 A1 | 3/2004 | Lee et al. |
| 2004/0172041 A1 | 9/2004 | Gresham et al. |
| 2004/0237785 A1 | 12/2004 | Neri |
| 2005/0043718 A1 | 2/2005 | Madhani et al. |
| 2005/0090811 A1 | 4/2005 | Doyle et al. |
| 2005/0169726 A1 | 8/2005 | McClure |
| 2005/0171470 A1 | 8/2005 | Kucklick et al. |
| 2006/0079884 A1 | 4/2006 | Manzo et al. |
| 2006/0161137 A1 | 7/2006 | Orban et al. |
| 2006/0235436 A1 | 10/2006 | Anderson et al. |
| 2007/0123798 A1 | 5/2007 | Rahamimov |
| 2007/0123855 A1 | 5/2007 | Morley et al. |
| 2007/0137371 A1 | 6/2007 | Devengenzo et al. |
| 2007/0156121 A1 | 7/2007 | Millman et al. |
| 2007/0239172 A1 | 10/2007 | Lee et al. |
| 2007/0267026 A1 | 11/2007 | Grant-Jennings |
| 2008/0033453 A1 | 2/2008 | Brock et al. |
| 2008/0065098 A1 | 3/2008 | Larkin |
| 2008/0188715 A1 | 8/2008 | Fujimoto |
| 2009/0030443 A1 | 1/2009 | Buser et al. |
| 2009/0105727 A1 | 4/2009 | Doyle et al. |
| 2009/0182351 A1 | 7/2009 | Malinowski |
| 2009/0248039 A1 | 10/2009 | Cooper et al. |
| 2009/0294313 A1 | 12/2009 | Pacey et al. |
| 2010/0063359 A1 | 3/2010 | Okoniewski |
| 2010/0241136 A1 | 9/2010 | Doyle et al. |
| 2011/0178531 A1 | 7/2011 | Caputo et al. |
| 2011/0319911 A1 | 12/2011 | Conner et al. |
| 2012/0010611 A1 | 1/2012 | Krom et al. |
| 2012/0010628 A1 | 1/2012 | Cooper et al. |
| 2012/0083799 A1 | 4/2012 | Chen et al. |
| 2012/0118098 A1 | 5/2012 | Doyle et al. |

\* cited by examiner

STERILE DRAPE HAVING MULTIPLE DRAPE INTERFACE MECHANISMS

CROSS-REFERENCE TO RELATED APPLICATIONS

This application is related to U.S. patent application Ser. No. 12/336,950 entitled Hand-Actuated Articulating Surgical Tool, by Mark C. Doyle, assigned to the assignee of the present invention, filed Dec. 17, 2008, now patented as U.S. Pat. No. 8,105,319. This application is also related to pending U.S. patent application Ser. No. 12/869,717 entitled Control Portion of and Device for Remotely Controlling an Articulating Surgical Instrument, by Craig Conner et al., assigned to the assignee of the present invention, filed Aug. 26, 2010.

FIELD

The invention relates generally to surgical instruments. More particularly, the invention relates to drape.

BACKGROUND

Current laparoscopic surgical tools are limited in accessibility of certain regions of the human body. Existing tools can perform invasive surgery without making a substantial incision, but these tools are incapable of bending within the body to reach.

Additionally, existing tools rely on use of cables to manipulate the surgical tip of the tool. These tools have the disadvantage of requiring extensive sterilization of the internal components. The cleaning of internal metal cables can be a lengthy and expensive process. This process must be repeated prior to each procedure. Alternatively, disposable components may be used with a substantial increase in recurring costs.

BRIEF DESCRIPTION OF THE DRAWINGS

FIG. 2 is a detailed drawing of one embodiment of the control portion of the invention.

FIG. 3A shows the cylinder's retracted position, while FIG. 3B shows the cylinder's extended position. FIG. 3C shows the front view of the cylinder. FIG. 3D shows the components of the control cylinder individually.

FIG. 4A shows the module's retracted position, while FIG. 4B shows the module's extended position. FIG. 4C shows the front view of the module. FIGS. 4D-E show two embodiments of an electrical extend module.

FIG. 7A is top view and FIG. 73 is side view.

FIG. 9 depicts various arrangements of the modules.

FIG. 10A shows the guide tubes as they are attached to the cannula using an elastic strap. FIG. 103 shows the position of the guide tubes with respect to the bend module, while FIG. 10C shows the position of the guide tubes with respect to the extend module.

FIG. 12 shows an embodiment of the tissue restraint module. FIG. 12A is top view while FIG. 123 is side view.

DESCRIPTION OF EMBODIMENTS

Certain embodiments of the invention will now be described in detail with reference to the figures.

Figure 1:
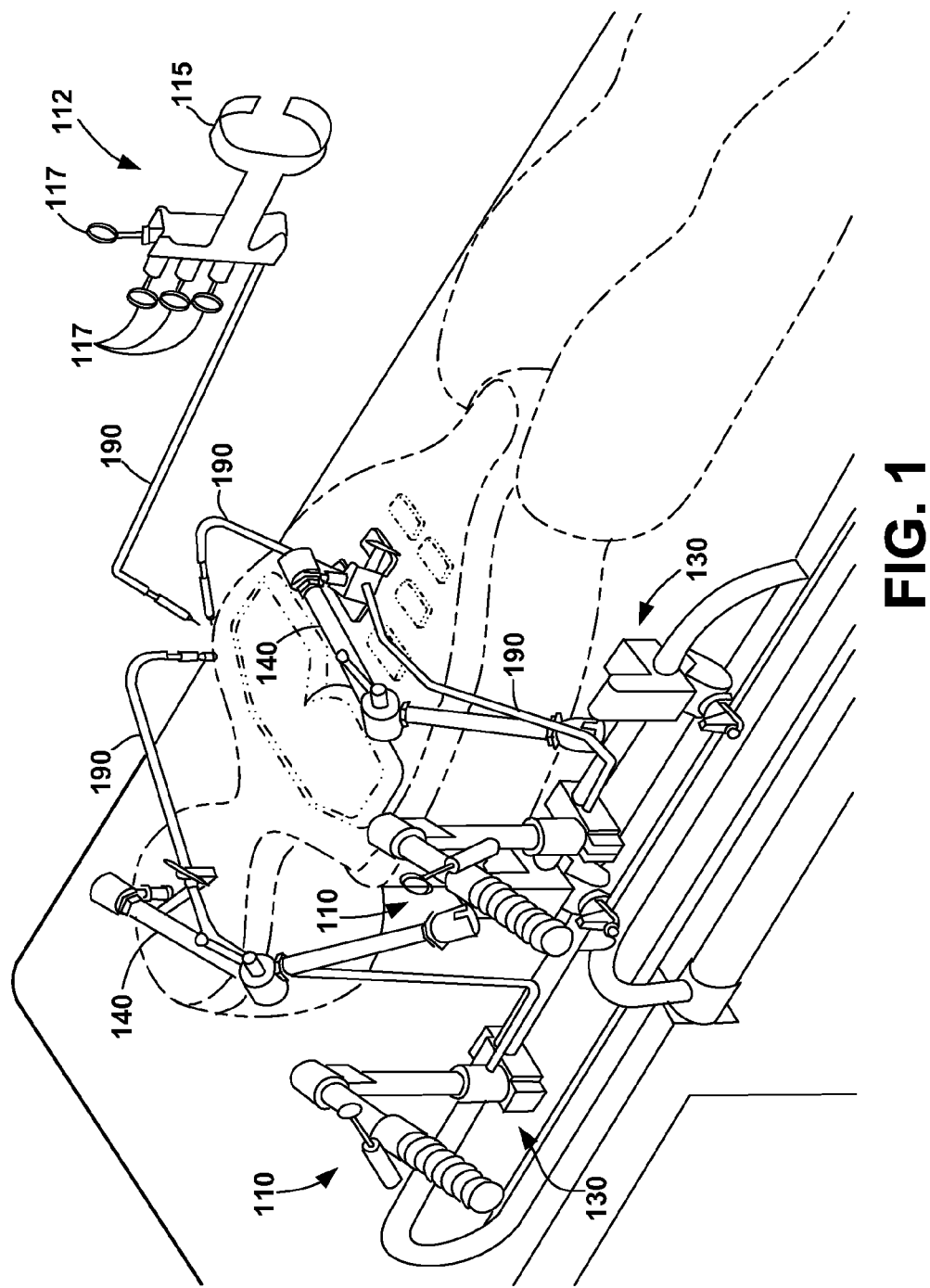
FIG. 1 is an overview of one embodiment of the invention.

FIG. 1 shows a surgical tool according to the present invention. The tool has a control portion 110, 112 at the proximal end of the device and a slave portion 120 at the distal end of the device. As used herein, "proximal" refers to the part of the device that remains outside the patient's body, closest to the user. "Distal" refers to the end inserted into the patient, farthest away from the user. As with a specific component of the device, "proximal" refers to the part of the component closest to the proximal end of the device, whereas "distal" refers to the part of the component closest to the distal end of the device. An intermediate portion 190 lies between the control portion 110 and the slave portion 120. The "slave portion," or the "distal end of the device," 120 is the portion of the device comprising the slave modules, i.e., the extend module, the bend module, the rotate module, and the grasp module, as each is described in greater detail below. Each portion will now be described in greater detail. The term "cannula" is used to refer to the portion of the device comprising both the intermediate portion 190 and the slave portion 120.

The control portion 110, 112 may be any device that can translate the movements of the user's hand and fingers into hydraulic, mechanical, or electrical signals to actuate the corresponding parts of the slave portion 120 of the device. For example, two such devices are shown in FIG. 1.

In certain embodiments, the control portion 110, 112 uses hydraulic fluid to transfer pressure from a control cylinder to a slave cylinder. The fluid is preferably sterilized distilled water, however a saline solution, a perfluorinated hydrocarbon liquid, or any other physiologically compatible fluid could also be used. A "physiologically compatible fluid" is a fluid that once exposed to tissues and organs, does not create any intolerable reaction, such as a rash or immune response, in the patient, and does not adversely interfere with the normal physiological function of the tissues or organs to which it is exposed. In addition, a physiologically compatible fluid can remain in a patient's body or in contact with a tissue or an organ without the need to remove the fluid.

In one embodiment, the control portion 112 clamps onto the arm of the user by way of a clamp 115. The control portion 112 features finger loops 117, into which the user inserts the user's fingers. By squeezing each finger loop 117, the user creates hydraulic pressure or an electrical signal that results in a corresponding motion at the distal end 120 of the device. The user may then "open" the squeezed finger to create the opposite motion.

Figure 3A:
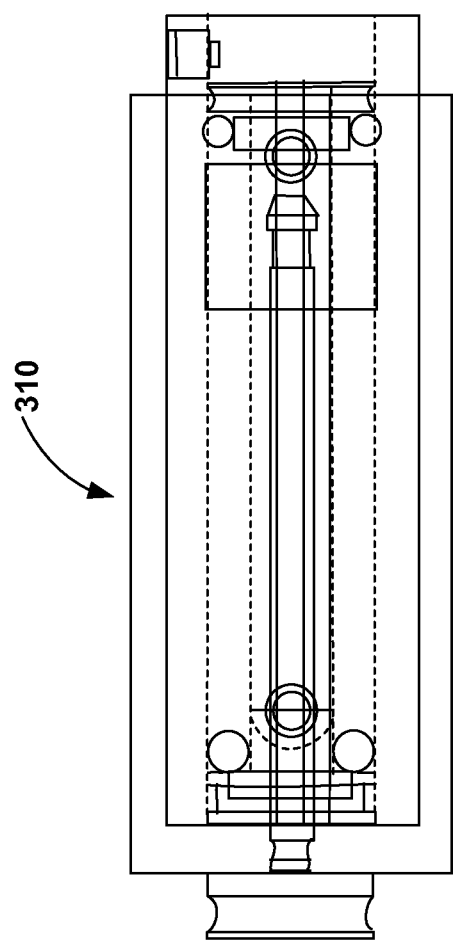
FIGS. 3A-D are detailed drawings of an embodiment of a control cylinder.

Each finger loop 117 is connected with a control cylinder 310 (shown in FIG. 3A). The finger loop 117 should be large enough to allow comfortable insertion of a human finger. The finger loop 117 is connected to a longitudinal shaft. The shaft may be made of, for example, metal, ground glass, or ceramic. The shaft may be of any cross-sectional shape. In one embodiment, a circular cross-section is used. The cross-sectional size of the shaft, along with the material, are designed to provide sufficient stiffness for predictable control when the finger loop 117 is moved. The shaft slides through an opening in the end of the cylinder body. The interface between the shaft and the opening in the end of the cylinder body is formed to allow for smooth forward and backward movement of the shaft and, at the same time, to provide a waterproof seal.

Another embodiment of the invention includes a control portion 110 that is clamped to the side of a surgical bed using clamps 130. In this embodiment, the user grasps the control portion 110 much in the same way that a motorcycle driver grasps the handles of a motorcycle. The user may turn the handles, push them in, pull them out, pivot them about their axes, or, with the aid of a thumb loop, squeeze them. As detailed below, each of these motions creates a corresponding motion at the distal end 120 of the device.

In another embodiment, the control portion 110 is clamped to an object other than the surgical bed, such as a table or a cart. In yet another embodiment, the control portion 110 is clamped to the user's arms or hand. In still another embodiment, the control portion 110 is held by the user, without it being clamped to anything.

Figure 2A:
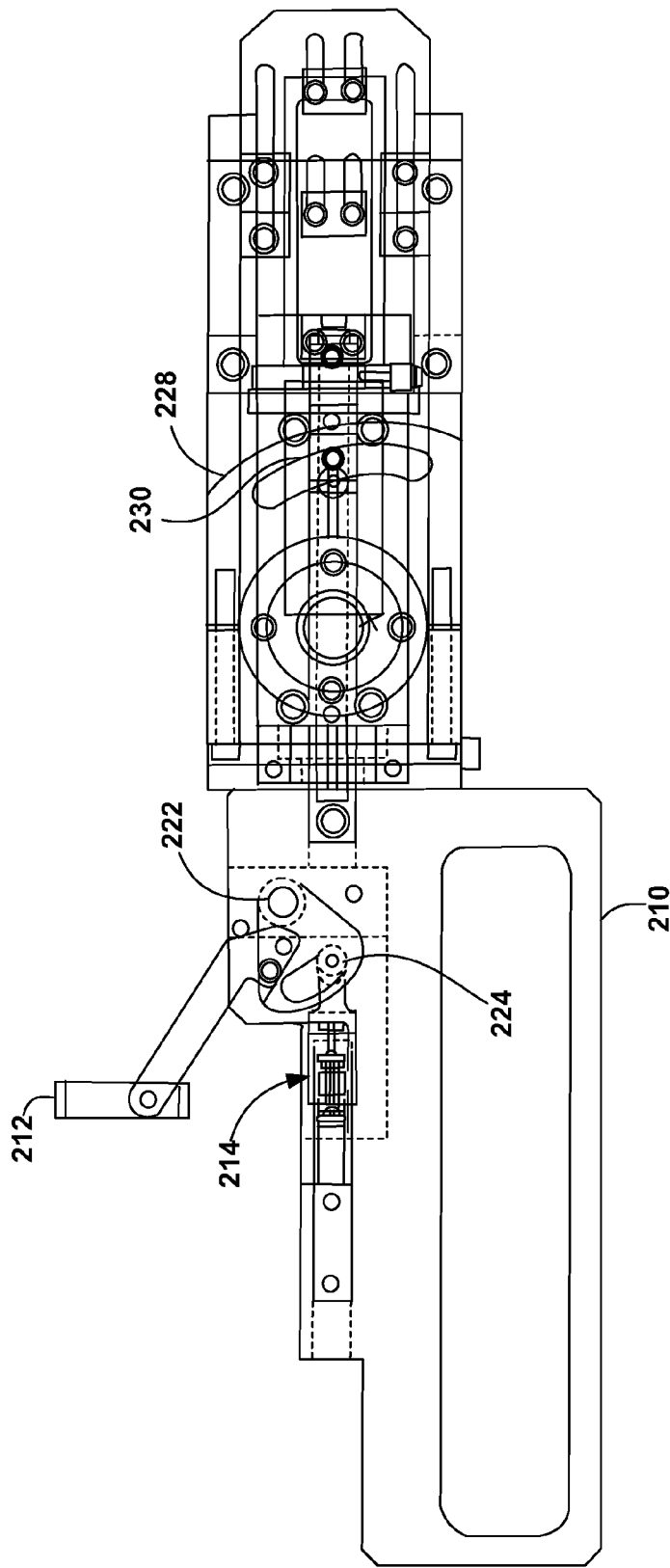
FIG. 2A is top view.

FIG. 2A shows the top view of the control portion 110. A handle 210 is provided for the user's fingers to pass through, while the user's thumb is inserted through a thumb loop 212. The handle 210 may exhibit ridges on the inside of the open loop in order to more comfortably accommodate a user's fingers.

The movements of the control portion 110 are translated into hydraulic motion through the use of control cylinders 214, 216, 218, 220. When the user squeezes the thumb loop 212 towards the handle 210, a bend cam 222 is turned about a vertical axis. The bend cam 222 is shown in FIG. 2D. As the bend cam 222 turns, a roller 224 is pushed towards the back of the handle. The roller 224 is connected to an outer cylinder 312 of a control cylinder 214 via a shaft 318. The backward movement of the shaft 318 extends a piston 320 backwards, thereby creating the hydraulic pressure needed to actuate a slave cylinder in the distal end 120 of the device. The function of a control cylinder and its connection to a slave cylinder are discussed in greater detail below. In one embodiment of the invention, the squeezing of the thumb loop actuates a grasp function at the distal end 120.

The control portion 110 may be attached to the side of a surgical bed using a clamp 130. However, the control portion is free to rotate about a vertical axis 226, shown in FIG. 2B. The rotation of the control portion 110 about the axis 226 causes a roller 230 to move within a bend cam 228. The bend cam 228 is shown in FIG. 2E. The roller 230 is connected to an outer cylinder 312 of a control cylinder 220 via a shaft 318. The forward movement of the shaft 318 extends the piston 320 forward, thereby creating the hydraulic pressure needed to actuate a slave cylinder in the distal end 120 of the device. In one embodiment of the invention, the turning of the handle results in a rotation of the distal end 120 of the device through a rotate module, described in detail below.

A user may also push the handle 210 forward, in which case, the top portion of the control portion 110 moves forward over a slide 232. The side 232 is connected to an outer cylinder 312 of a control cylinder 218 via an attachment point 330. The outer cylinder 312 is in turn attached to the piston 320 via a shaft 318. The forward movement of the shaft 318 extends the piston 320 forward, thereby creating the hydraulic pressure needed to actuate a slave cylinder in the distal end 120 of the device. In one embodiment of the invention, the forward movement of the handle results in an extension of the distal end 120 of the device through an extension module, described in detail below.

Figure 2B:
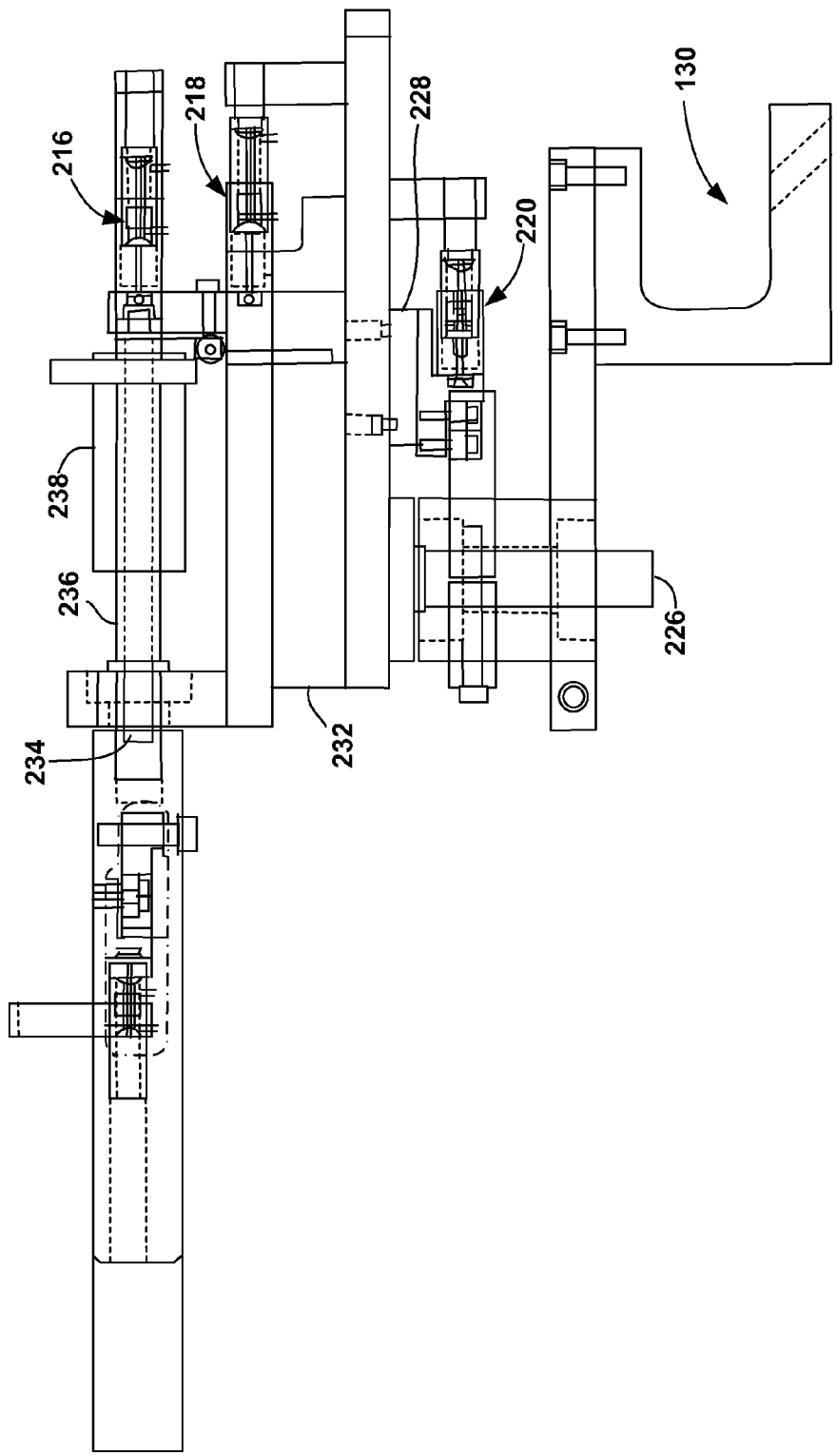
FIG. 2B is side view.
Figure 2C:
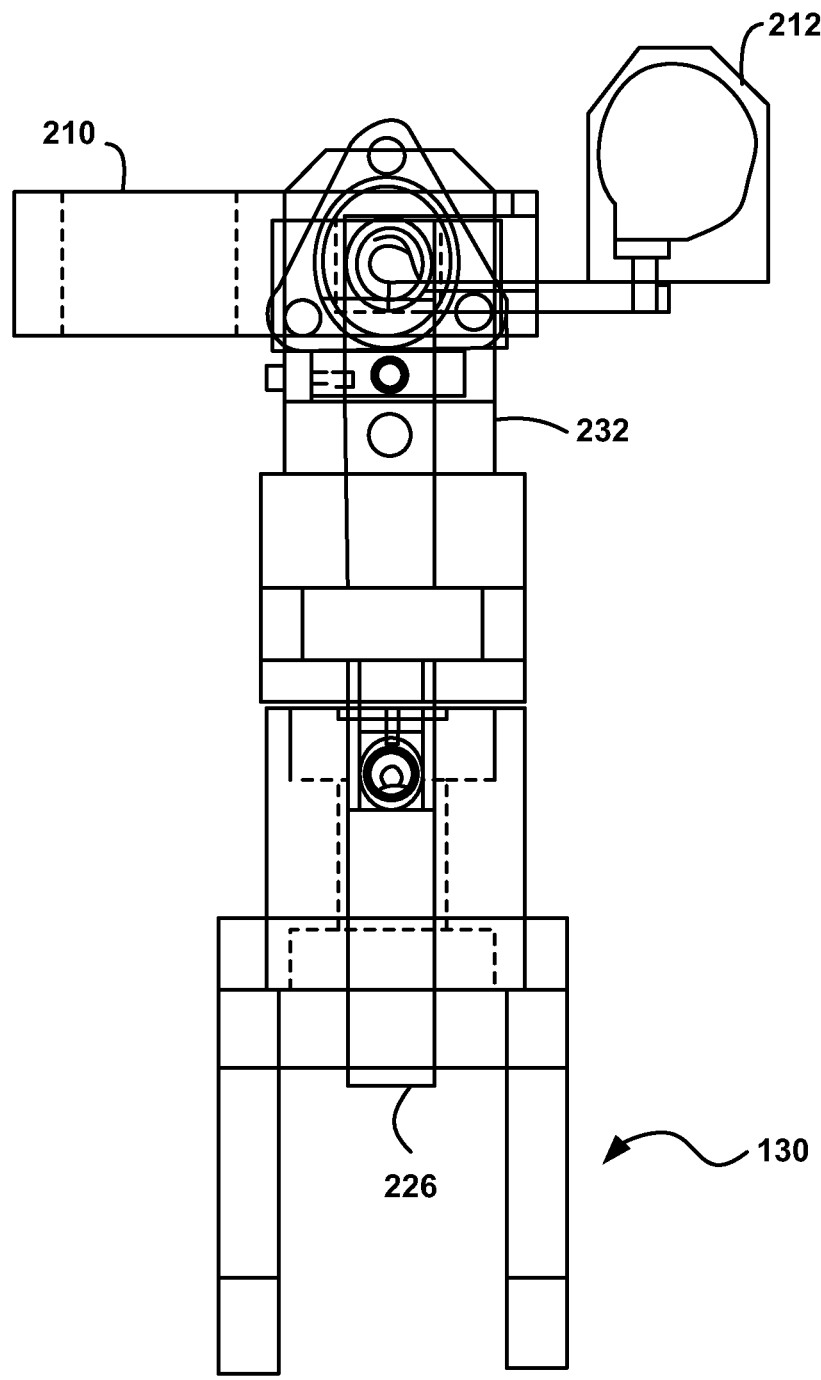
FIG. 2C is front view.
Figure 2D:
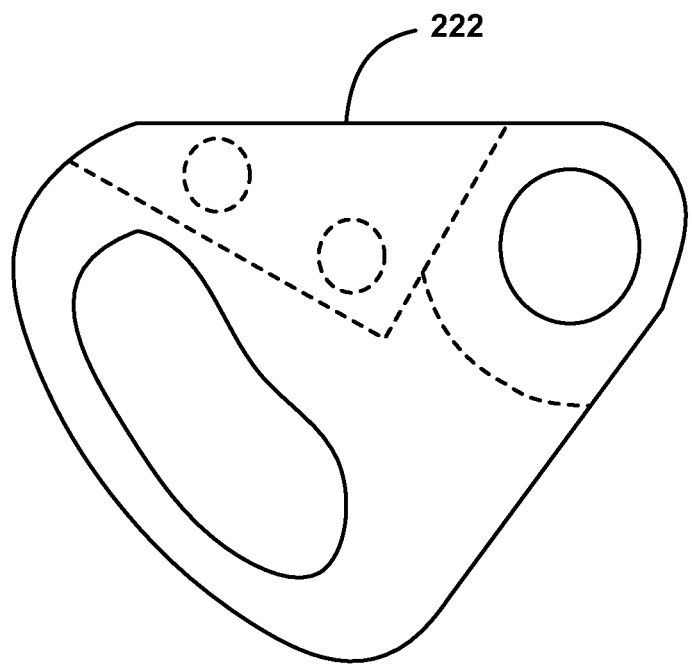
FIG. 2D shows a top view of a grasp cam.
Figure 2E:
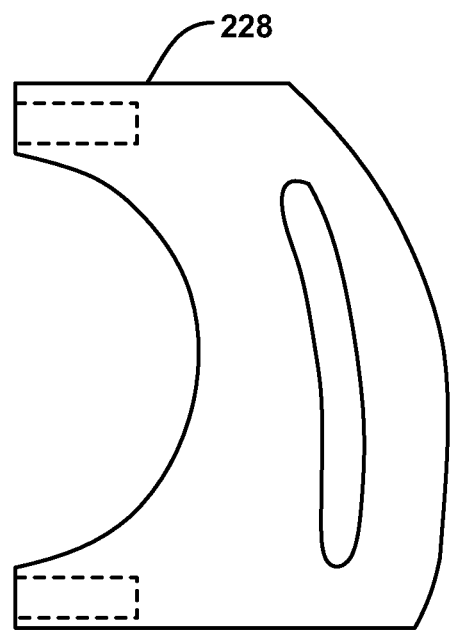
FIG. 2E shows a top view of a bend cam.

The handle part of the control portion 110 may also rotate along a longitudinal axis coinciding with the shaft 234, as shown in FIG. 2B. In certain embodiments of the invention, the turning of the handle part causes a screw 236 to rotate within a nut 238. In some embodiments of the invention, the screw 236 is stationary and the nut 238 is mobile, whereas in other embodiments of the invention, the screw 236 is mobile and the nut 238 is stationary. The movement of the screw 236 within the nut 238 causes the mobile unit to move linearly with respect to the stationary unit. The mobile unit, whether the screw or the nut, is connected to an outer cylinder 312 of a control cylinder 216 via an attachment point 330. The outer cylinder 312 is in turn attached to the piston 320 via a shaft 318. The forward movement of the shaft 318 extends the piston 320 forward, while the backward movement of the shaft 318 pulls the piston 320 backward. The forward and backward motion of the piston 320 creates the hydraulic pressure needed to actuate a slave cylinder in the distal end 120 of the device. In some embodiments of the invention, rotation of the handle part results in the rotation of the distal end 120 of the device through a rotation module, described in detail below.

In certain embodiments of the invention, the movements of the different parts of the control portion 110 creates electrical signals that are sent through wires in the intermediate portion 190 to the slave cylinders in the distal end 120 of the device. The electrical signal is sufficient to actuate motor in the corresponding slave cylinder, which in turn results in the slave module being actuated. Thus, for example, a forward movement of the handle 210 creates an electrical signal that actuates a motor in an extend module, which results in the extension of that module. Similarly, the rotation of the handle 210, the bending of the handle 210, and the squeezing of the thumb loop 212, result in the rotate module, the bend module, and the grasp module, respectively, being actuated. The slave modules having a motor are described in greater detail below.

Cylinders 214, 216, 218, and 220 are control cylinders. A typical control cylinder 310 is shown in its retracted position in FIG. 3A and in its extended position in FIG. 3B. The control cylinder 310 comprises an outer cylinder 312 and an inner cylinder 314. The inner cylinder 314 has a diameter that allows it to move within the outer cylinder 312. The outer cylinder 312 is connected to a shaft 318, which in turn is connected to the control portion 110 through the attachment point 330. The movements of the control portion 110, described above, causes the outer cylinder 312 to move longitudinally with respect to the stationary inner cylinder 314.

A piston 320, attached to a shaft 318, moves within the inner cylinder 314, within a distance defined by the two inlet points 322, 324 for the hydraulic fluid. The distal end of the shaft 318 is configured to be capable of attachment to the piston 320, while the proximal end of the shaft 318 is configured to be capable of attachment to the outer cylinder at a site dose to the attachment point 330. The outer cylinder or the handle assembly may be provided with ratchet teeth. The ratchet teeth are adapted to engage with a locking mechanism to secure the piston 320 at a desired position relative to the cylinder body. Alternatively, a locking mechanism may employ a friction lock to secure the piston 320 at a desired position.

The piston 320 has a solid front face and is movable along the longitudinal axis of the inner cylinder 314. The front face of the piston 320 is identical in shape to the cross section of the cylindrical cavity. The outer surface of the piston 320 forms an airtight seal with the inner surface of the inner cylinder 314. Thus, the portion of the cavity on one side of the piston 320 does not communicate with the portion of the cavity on the other side of the piston 320. At the same time, the piston 320 must be allowed to move smoothly back and forth along the longitudinal axis of the inner cylinder 314.

The proximal end of the inner cylinder 314 is sealed with a seal 316, comprising an opening there through, through which the shaft 318 can slide. The distal end of the inner cylinder 314 is sealed with another seal 328, optionally comprising an O-ring 326.

Figure 3B:
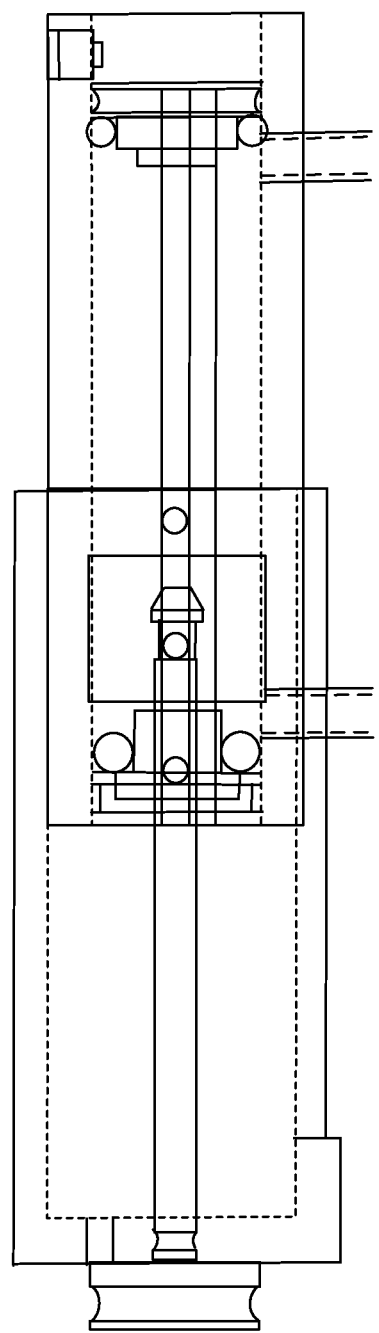
Figure 3C:
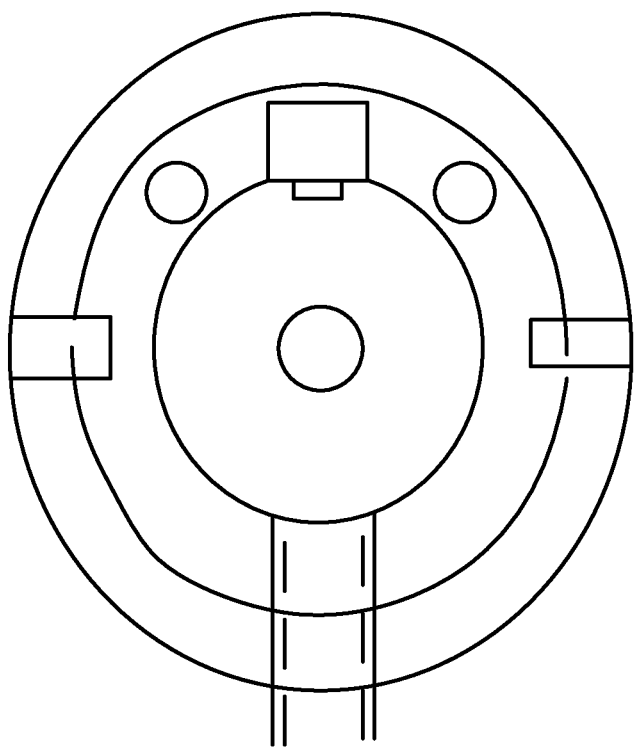
Figure 3D:
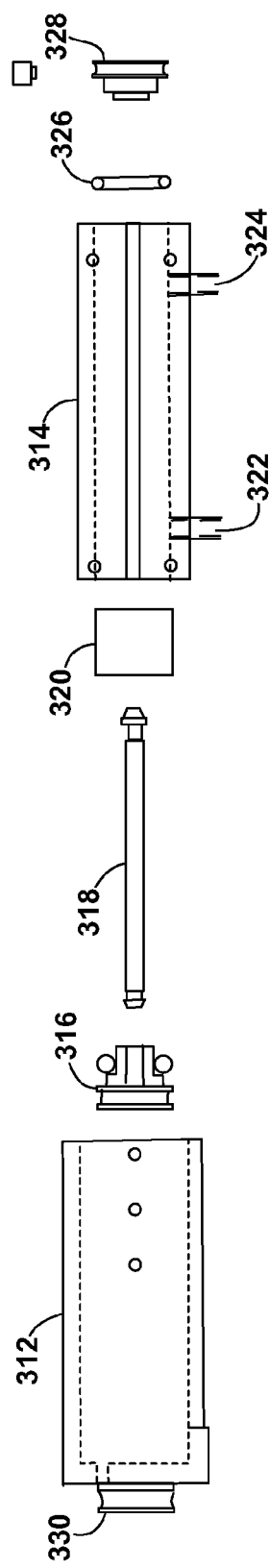

Thus, in the extended position of the control cylinder 310, FIG. 3B, the piston 320 is at rest against the proximal seal 316. The hydraulic fluid is located in the inner cylinder 314 in front of the piston 320. When the control portion 110 is moved in a way described above, when the handle 210 is moved forward, the outer cylinder 312 moves forward, thereby moving the shaft 318 and the piston 320. Hydraulic fluid exits the inner cylinder 314 through an inlet 324, creating a hydraulic pressure at a point in the distal end 120 of the device. Additional hydraulic fluid, displaced from a slave cylinder, enters to the back of the piston 320 through another inlet 322, thereby keeping the volume of the hydraulic fluid in the system constant. When the control portion 110 is moved completely, the control cylinder 310 is in its retracted position, FIG. 3A. In this position, the piston 320 is at the distal end of the inner cylinder 314, resting against the distal seal 328. The hydraulic fluid is in the back of the piston 320. Those of skill in the art understand that although in the above discussion the piston 320 is described to move from the fully retracted position to the fully extended position, the piston 320 may move from any point along the two extremes to any other point along the two extremes, and thereby cause a corresponding movement in a slave cylinder.

The cannula 190 comprises hydraulic tubings, connecting the control cylinders of the control portion 110 with the slave cylinders at the distal end 120, and housings for the hydraulic tubings.

The distal end 120 comprises modular components. The components can be selected from, for example, an extend module, a rotate module, a bend module, and a grasp module. Other functions can be included as well and activated in the manner described in detail below. Each module is individually describe in greater detail below. The invention is adapted such that the user can pick the combination of modules and the quantity of each individual module that is best suitable for the user's needs and assemble them conveniently.

Figure 4A:
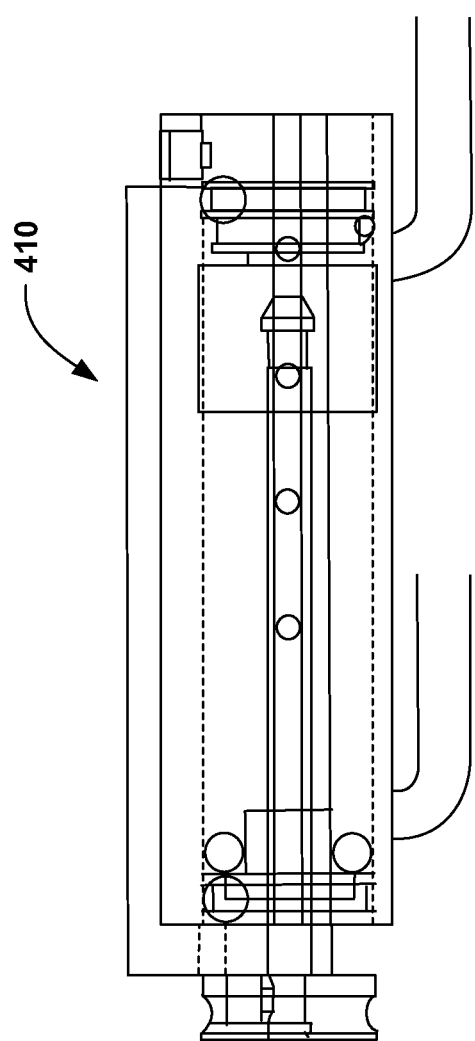
FIGS. 4A-E are detailed drawings of an embodiment of a hydraulic extend module.
Figure 4B:
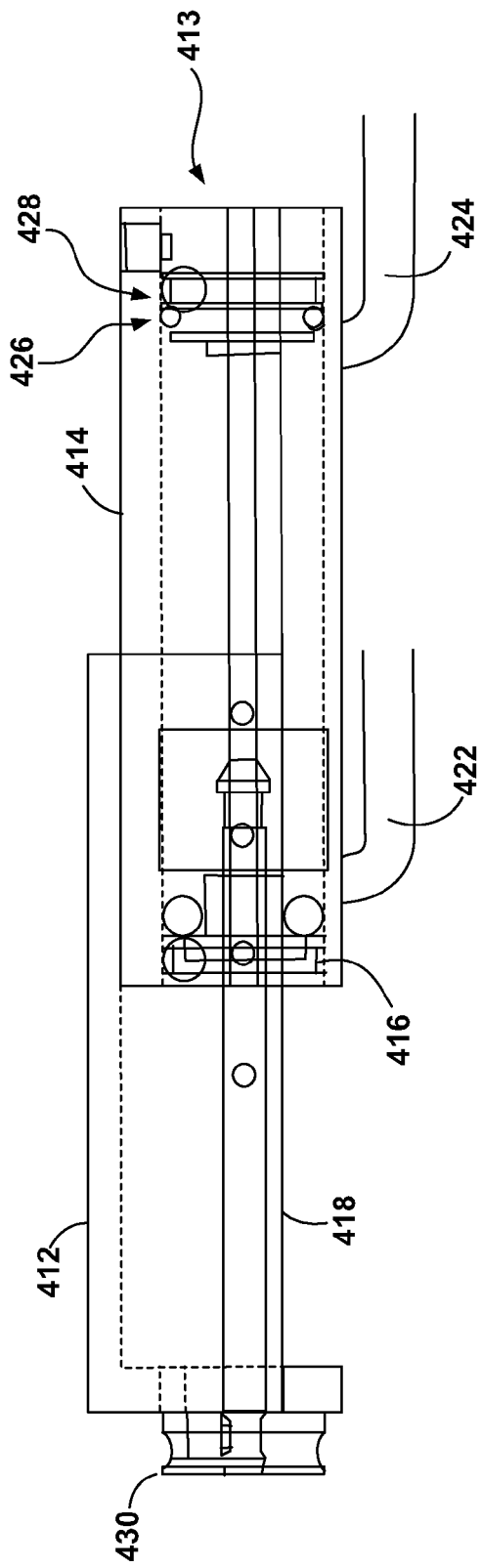

The extend module 410 is depicted in both its retracted position, FIG. 4A, and extended position, FIG. 4B. The extend module 410 is identical in its construction to the control module 310; however, the function of the two are reversed. By applying hydraulic pressure using the control portion 110, hydraulic fluid enters the inner cylinder 414 pushing the piston 420 towards the distal end of the r module and the distal seal 416. The shaft 418 moves through the distal seal 416, but it is attached to the outer cylinder 412 at the distal end of the outer cylinder 430. The movement of the piston 420 moves the outer cylinder 412 towards the distal end of the module, thereby extending the cannula. The hydraulic fluid present inside the inner cylinder 414 exits the inner cylinder 414 through the distal outlet 422. The proximal seal 428 prevents the leakage of hydraulic fluid from proximal end of the inner cylinder 414.

Additional modules can be attached to the extend module either at its distal end, through the distal attachment point 430, or at its proximal end, through the proximal attachment point 431.

In another embodiment, the extend module may be extended using electrical power instead of hydraulic power. In this embodiment, by pushing forward on the handle 210 of the control portion 110, the user causes an electrical connection to be formed, whereby electrical signal is sent from the control portion 110 through wires in the intermediate portion 190 to the extend module 432, FIGS. 4D, 4E. The electrical signal causes an electrical motor 434 to turn. In one embodiment, FIG. 4D, a screw 436 is mounted within the motor 434. The turning of the motor 434 causes the screw to move outward, thereby causing the outer cylinder 440 to move away from the inner cylinder 442. In this embodiment, the motor is stationary, i.e., it is attached to the inner cylinder 442, whereas the screw is mobile, i.e., it moves with respect to the motor and the inner cylinder 442. The screw 436 is attached at its distal end to the outer cylinder 440.

Figure 4C:
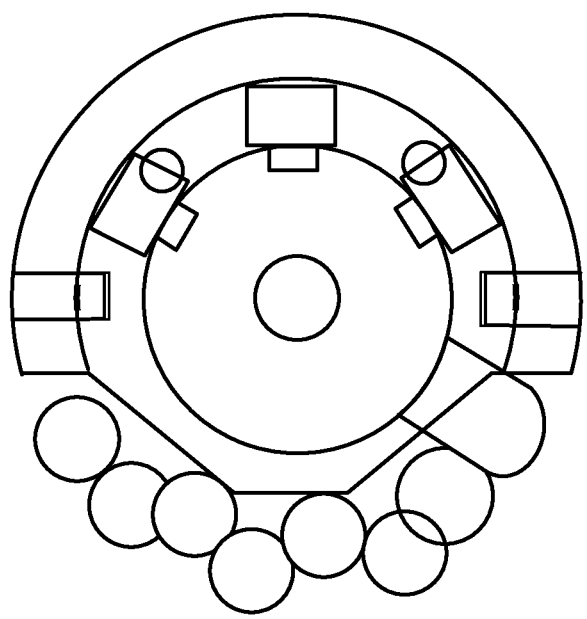
Figure 4D:
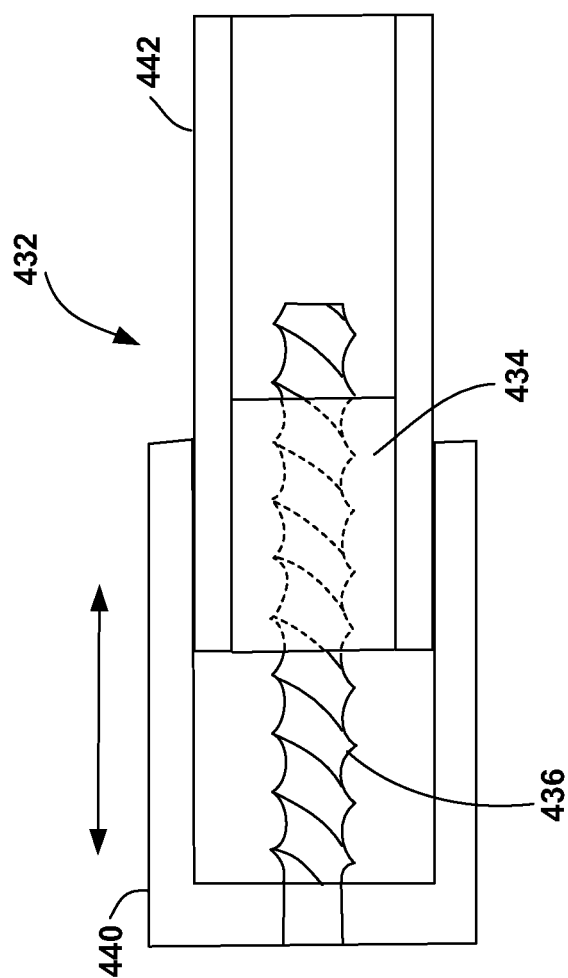
Figure 4E:
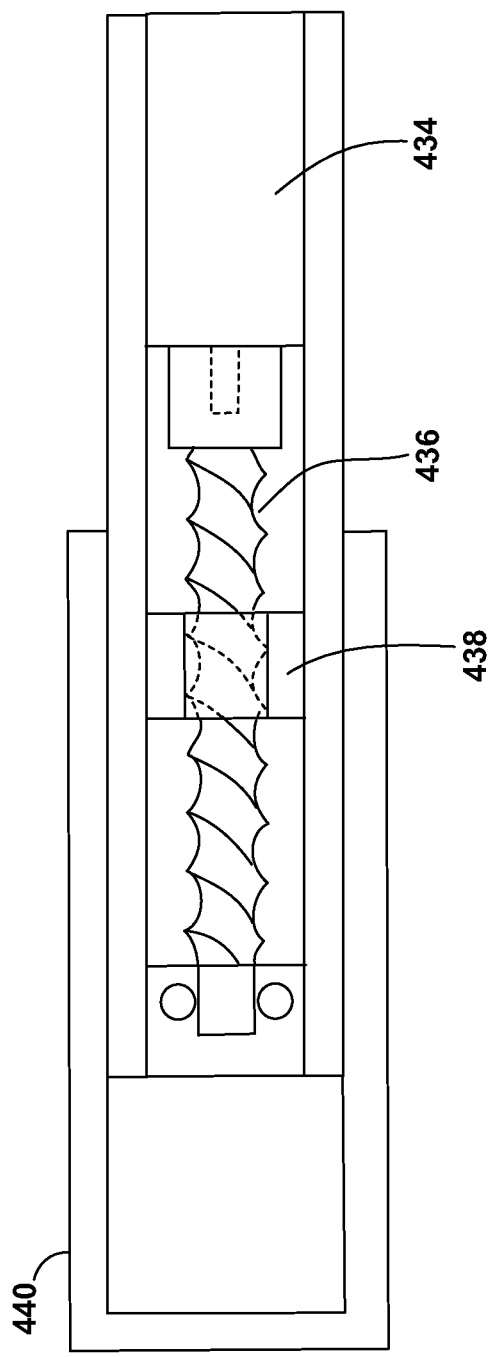

In another embodiment, FIG. 4E, the motor 434 causes the screw 436 to turn within a nut 438. The nut 438 is attached to the outer cylinder 440. The turning of the screw 436 causes the nut 438 to move with respect to the screw 436, thereby moving the outer cylinder 440 longitudinally with respect to the inner cylinder 442, causing the module to extend. In this embodiment, the motor 434 and the screw 436 are stationary with respect to the inner cylinder 442, whereas the nut 438 and the outer cylinder 440 are mobile.

Figure 5A:
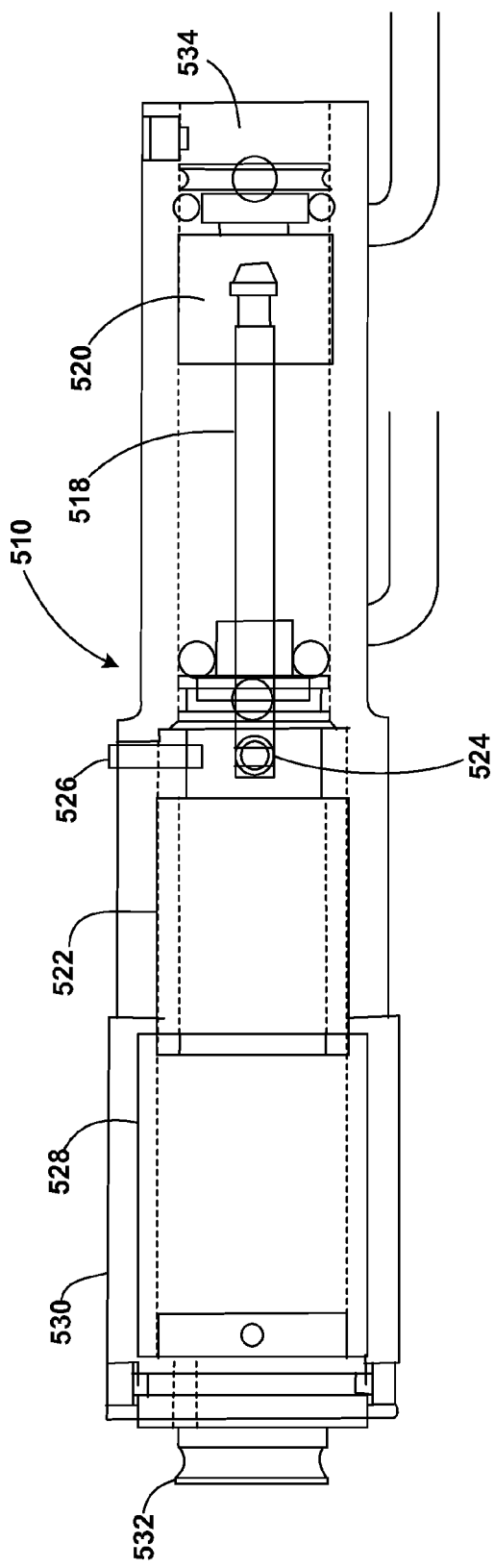
FIG. 5A is a detailed drawing of an embodiment of a hydraulic rotate module.

The rotate module 510, FIG. 5A, comprises similar hydraulic components as those of the extend module 410. As in the extend module 410, hydraulic pressure, applied by rotating the control portion 110 along a longitudinal axis, causes piston 520 to move toward the distal end of the module, causing the shaft 518 to move in that direction as well. The shaft 518 is attached to a lead screw 522 at an attachment point 524. Extension of the shaft 518 causes the lead screw 522 to move towards the distal end of the module. The lead screw is incapable of rotating, since a stabilizer 526 prevents its rotation. The lead screw 522 instead is extended through a nut assembly 528 which is immovably attached to an outer cylinder 530. The movement of the lead screw 522 through the nut assembly 528 causes the nut assembly 528 to rotate, thereby rotating the outer cylinder 530.

Additional modules can be attached to the rotate module either at its distal end, through the distal attachment point 532, or at its proximal end, through the proximal attachment point 534.

Figure 5B:
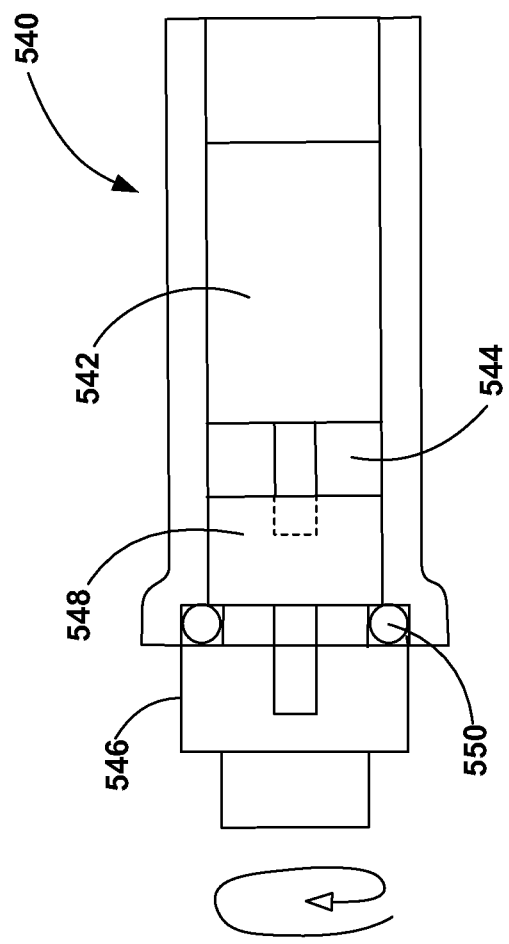
FIG. 5B is a detailed drawing of an embodiment of an electrical rotate module.

In another embodiment, the rotate module may be rotated using electrical power instead of hydraulic power. In this embodiment, by turning the handle 210 of the control portion 110, the user causes an electrical connection to be formed, whereby an electrical signal is sent from the control portion 110 through wires in the intermediate portion 190 to the rotate module 540, FIG. 5B. The electrical signal causes an electrical motor 542 to turn. The electrical motor 542 is attached to a shaft 544 which in turn is attached to the outer cylinder 546. The turning of the shaft rotates the outer cylinder. In some embodiments, a gear reducer assembly 548 may also be present to reduce the rotation speed. In certain embodiments, the connection between the outer cylinder 546 and the cylinder housing the motor assembly 542 may feature a bearing assembly 550.

Figure 6A:
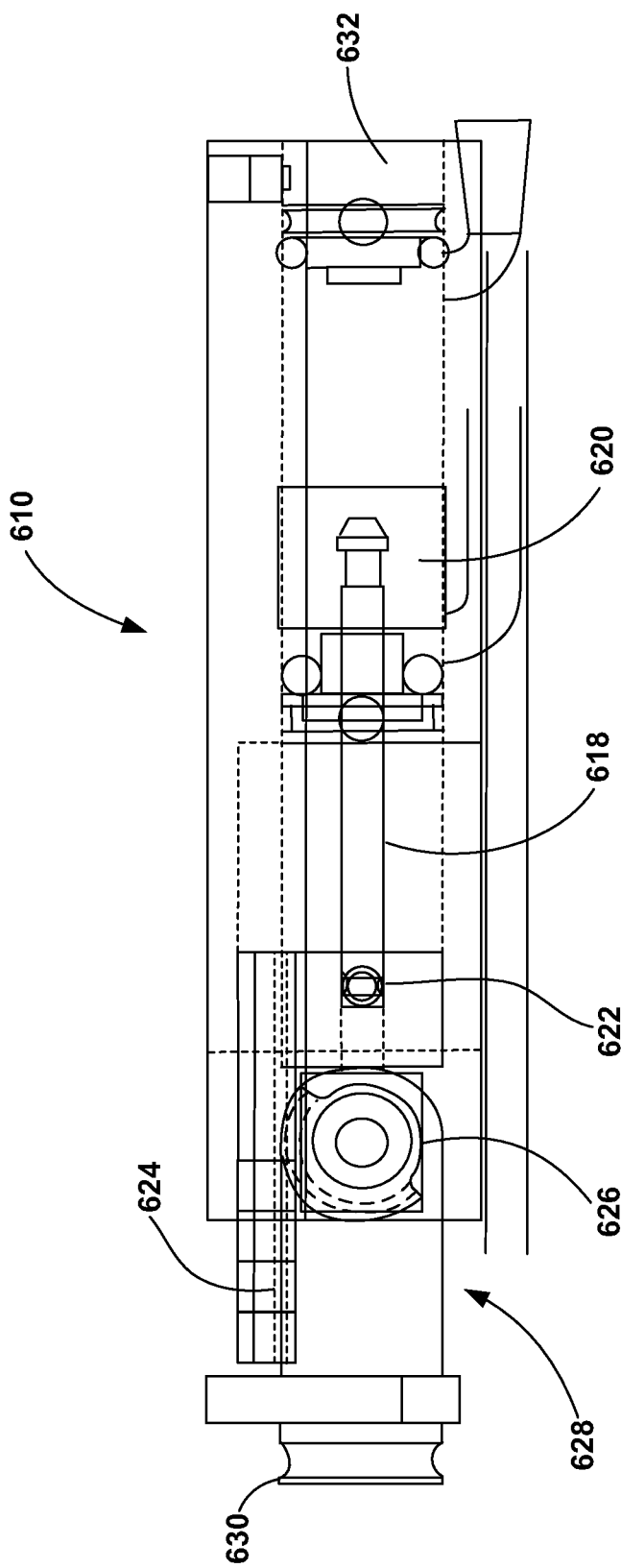
FIG. 6A is a detailed drawing of an embodiment of a hydraulic bend module.
Figure 6B:
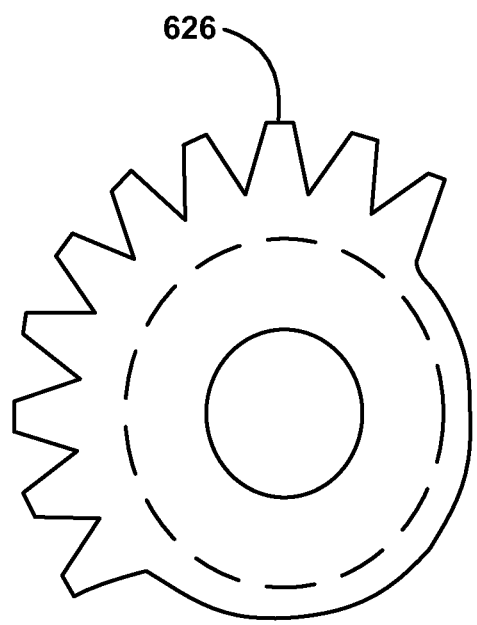
FIG. 6B is a drawing of a gear component in the module.
Figure 6C:
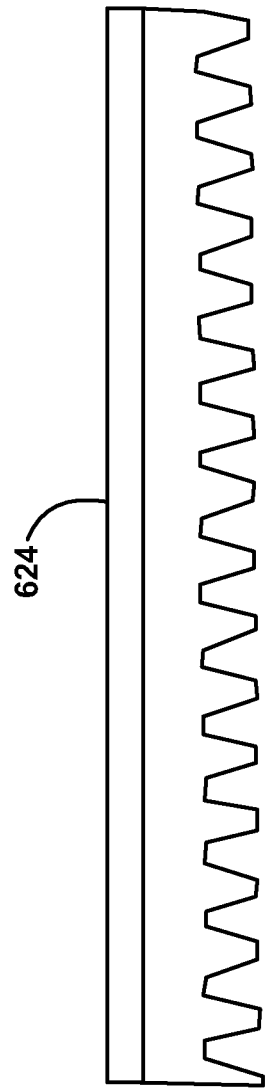
FIG. 6C is a drawing of a rack component in the module.

The bend module 610 is depicted in FIG. 6A. This module also features the same hydraulic assembly present in the extend and the rotate modules, above. Applying hydraulic pressure by rotating the control portion 110 along the vertical axis 226 in a clockwise direction causes the piston 620 and the shaft 618 to move towards the distal end of the module. The shaft 618 is attached to a rack 624 either directly or through an attachment assembly 622. The movement of the shaft 618 moves the rack 624. The rack 624 has teeth that correspond to the teeth on a gear 626. The movement of the rack 624 causes the gear 626 to rotate clockwise. The gear 626 is connected to the distal end 628 of the module. The rotation of the gear 626 causes the distal end 628 of the module to bend clockwise. By rotating the control portion 110 in a counter-clockwise direction, the piston 620 is moved towards the proximal end of the module, causing the rack 624 to move backwards as well, which in turn causes the gear 626 to turn counter-clockwise, which in turn causes the distal end 628 of the module to bend counter-clockwise.

In some embodiments, the bending of the distal end 628 of the module is through an angle of at least 110°, i.e., when the piston 620 moves from the proximal end of the hydraulic portion completely to the distal end of the hydraulic portion, the distal end 628 of the module bends at least 110°. In other embodiments, the rotation is an angle of at least 110°, at least 150°, at least 200°, at least 250°, at least 300°, or an angle of at least 350°.

Additional modules can be attached to the bend module either at its distal end, through the distal attachment point 630, or at its proximal end, through the proximal attachment point 632.

In another embodiment, the bend module may be bent using electrical power instead of hydraulic power. In this embodiment, by turning the handle 210 of the control portion 110, the user causes an electrical connection to be formed, whereby electrical signal is sent from the control portion 110 through wires in the intermediate portion 190 to the bend module. The electrical signal causes an electrical motor to turn. The electrical motor is attached to a shaft which in turn is attached to the rack 624. The movement of the shaft 618 moves the rack 624, which in turn causes the gear 626 to rotate, which in turn causes the distal end 628 of the module to bend.

Figure 6D:
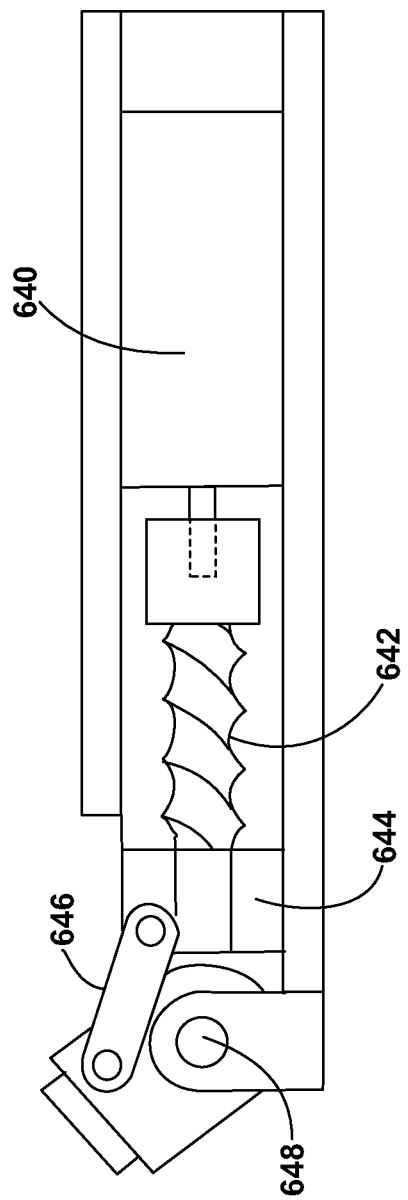
FIG. 6D is a detailed drawing of an embodiment of an electrical bend module.

In another embodiment, FIG. 6D, the turning of the motor 640 causes a lead screw 642 to rotate within a nut 644. The lead screw 642 is stationary with respect to the motor 640 and the outer body of the module, whereas the nut 644 is mobile. The nut 644 is connected to a link 646 at the proximal end of the link 646. The distal end of the link 646 is connected to the distal end of the module. When the nut 644 is moved backwards, it causes the link 646 to move backwards, thereby causing the distal end of the module to rotate. Reversing the electrical current, by rotating the control portion 110 in the opposite direction, will cause the motor to turn in the opposite direction, thereby causing the nut to move forward and the distal end of the module to bend in a clockwise direction.

Figure 7A:
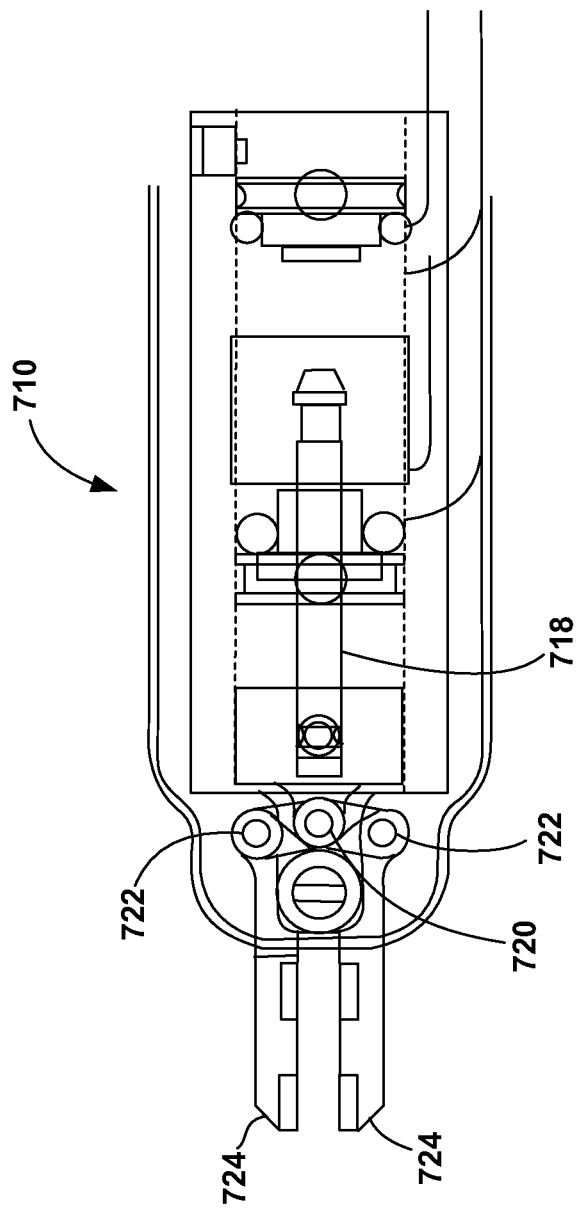
FIG. 7A-B is a detailed drawing of an embodiment of a hydraulic grasp module.
Figure 7B:
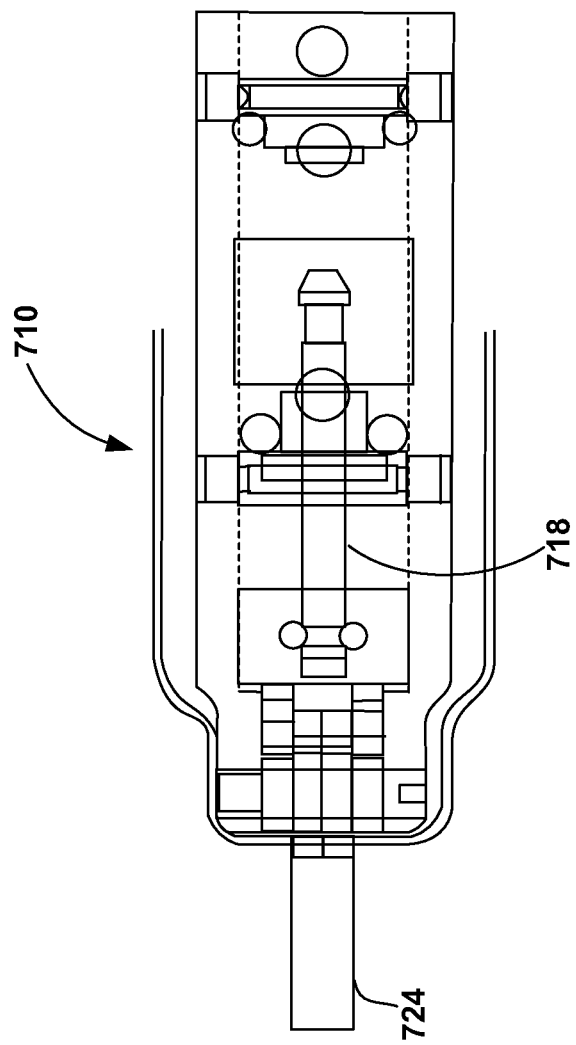

FIG. 7A depicts the top view of the grasp module 710, whereas FIG. 7B depicts its side view. The grasp module 710 also features a hydraulic portion similar to those of other modules. When the thumb loop 212 is squeezed towards the handle 210, hydraulic pressure is applied and the shaft 718 moves towards the distal end of the module. This movement causes the pin 720 to move towards the distal end of the module as well, thereby causing the two pins 722 to move away from the center. As the two pins 722 move away from the center, the angle defined by pin 722-pin 720-pin 722 tends away from 90° and towards 180°. The movement of the pins 722 causes the two tynes 724 to move towards each other and, eventually, touch. Moving the thumb loop 212 away from the handle 210 will have the opposite effect of causing the tynes 724 to move away from each other and open up.

Figure 7C:
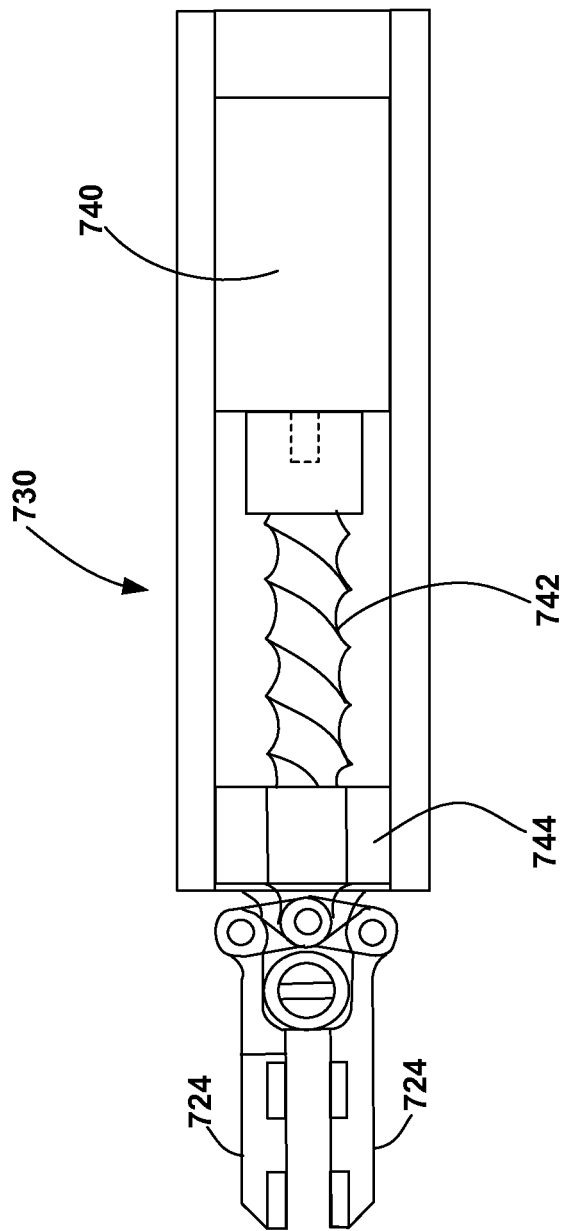
FIG. 7C is a detailed drawing of an embodiment of an electrical grasp module.

In another embodiment, the squeezing of the thumb loop 212 causes an electrical current to turn a motor 740, FIG. 7C, in the grasp module 730. The motor 740 turns a stationary lead screw 742, which in turn causes a nut 744 to move longitudinally. The movement of the nut 744 causes the tynes to move closer to each other and, eventually, touch. Moving the thumb loop 212 away from the handle 210 will have the opposite effect of causing the tynes 724 to move away from each other and open up.

Figure 8:
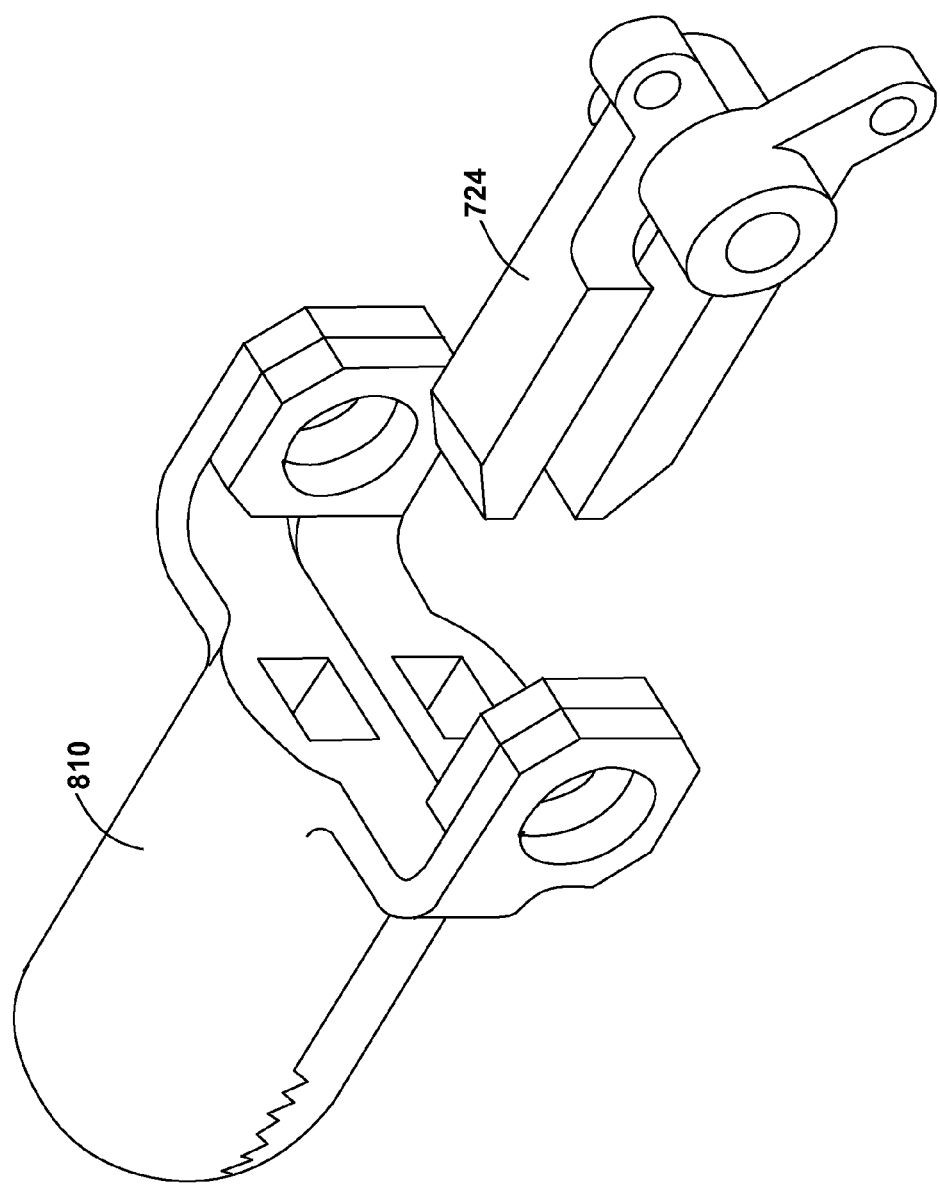
FIG. 8 depicts a tool adapted to fit over the tynes of a grasp module.

The tynes 724 of the grasp module 710 are configured to accommodate a number of different tools. For example, in FIG. 8, a grasp tool 810 is shown that can fit over the tynes 724. When the tynes 724 move towards each other, the end portion of the grasp tool 810 also move toward each other and, eventually, touch. If an object or tissue is located between the end portions of the grasp tool 810, the object is then grasped by the tool. There may be a number of tools that can be attached over the tynes 724. In addition to the grasp tool, these include a scissors, a knife for cutting the tissue, drill bits for drilling into bones, heating elements for cauterizing tissue, or any other tool necessary during a surgical procedure.

All the above tools and other tools can fit individually and interchangeably on the grasp module 710. Therefore, during a surgical procedure, the user may attach one tool to the grasp module 710, use it, remove it, and then attach another tool to the same grasp module 710. This process can be repeated any number of times with any number of tools.

Figure 9A:
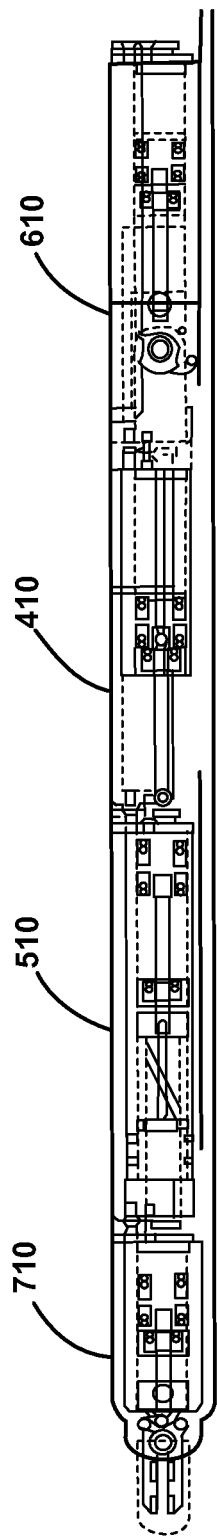
FIG. 9A shows the modules in bend-extend-rotate-grasp configuration, with the bend module in the straight conformation.
Figure 9B:
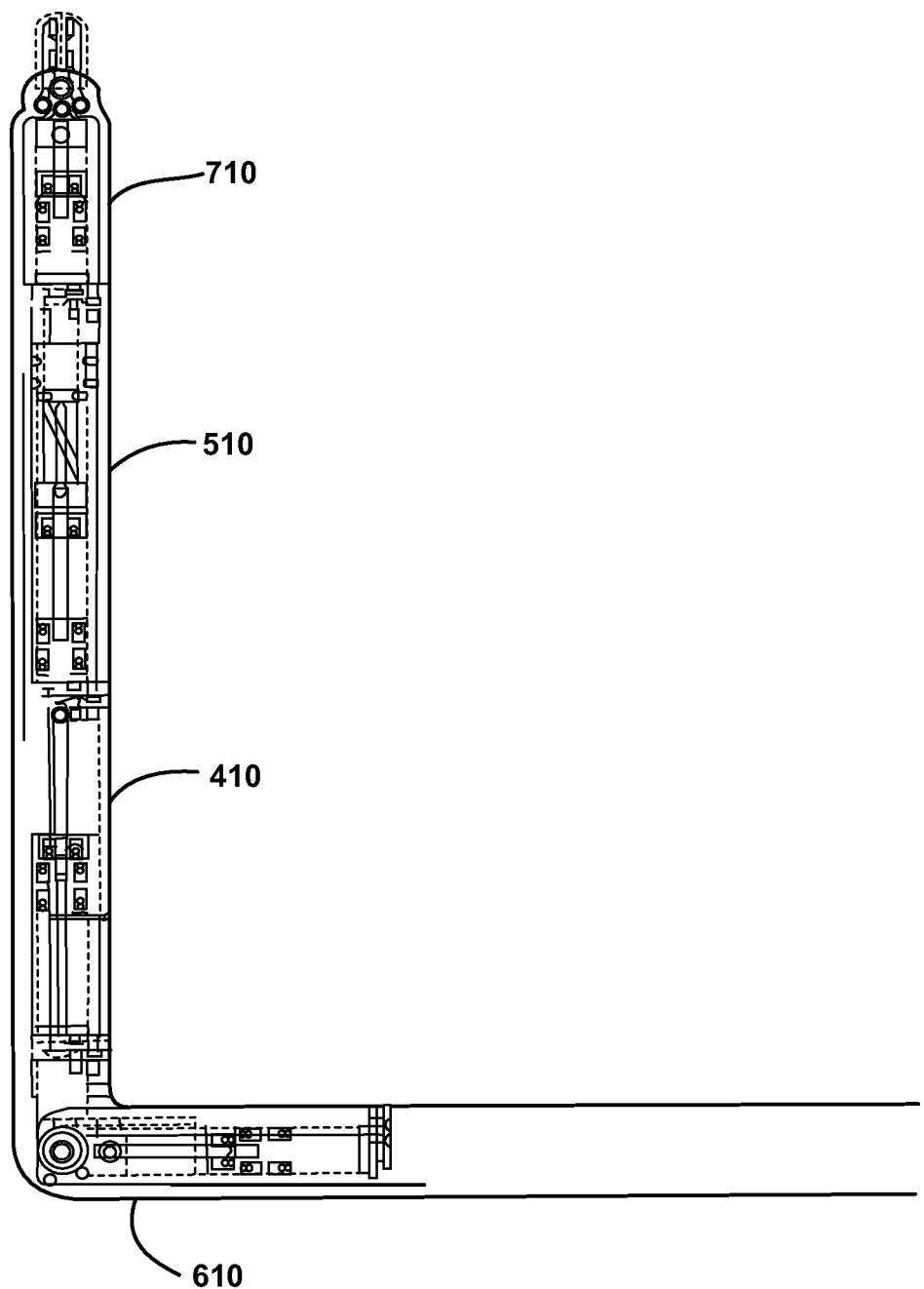
FIG. 9B shows the same arrangement with the bend module in the bent conformation.
Figure 9C:
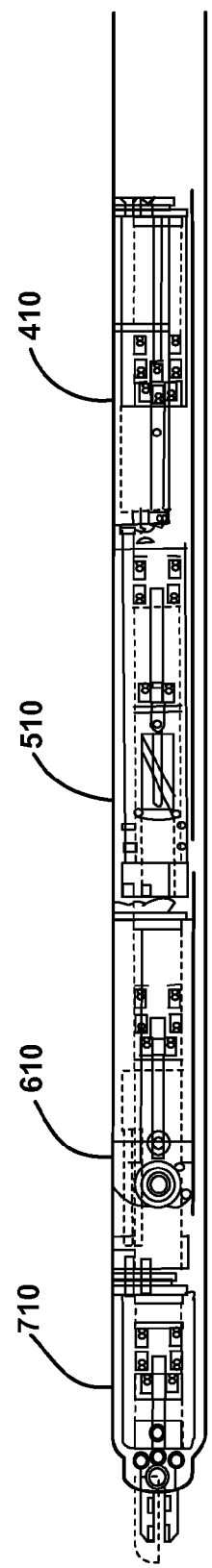
FIG. 9C shows the modules in extend-rotate-bend-grasp configuration, with the bend module in the straight conformation.
Figure 9D:
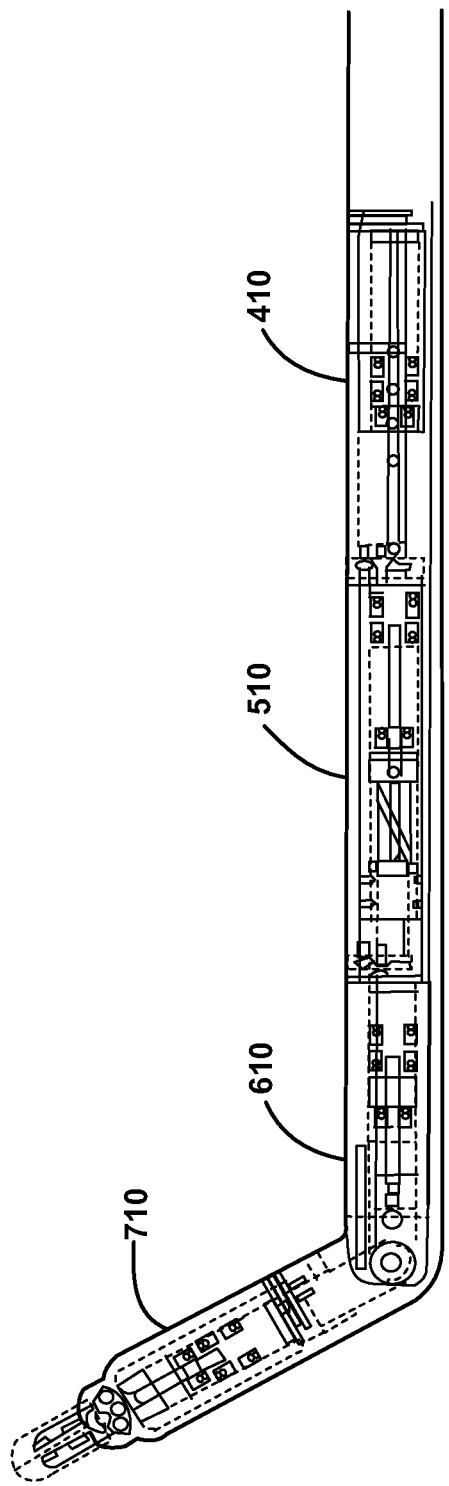
FIG. 9D shows the same arrangement with the bend module in the bent conformation.

As mentioned above, the modules of the present invention are designed to be placed in order that the user deems most useful. For example, FIGS. 9A-D depict four of the modules attached in the order of (from proximal end to distal end) bend, extend, rotate, and grasp. FIG. 9A shows the bend module in its retracted position, where the cannula is straight. FIG. 9B shows the bend module in its extended position where the module is bent. Alternatively, the four modules could be arranged in the extend-rotate-bend-grasp configuration, as shown in FIGS. 9C, 90. Other combinations are also possible. In addition, the user may attach more than a single module of a particular type, for example, two or three or more extend modules or two or three or more bend modules, could be put together, along with other nodules to form the distal end 120 of the device. Preferably, the grasp module 710 is always the most distally located module.

Figure 10A:
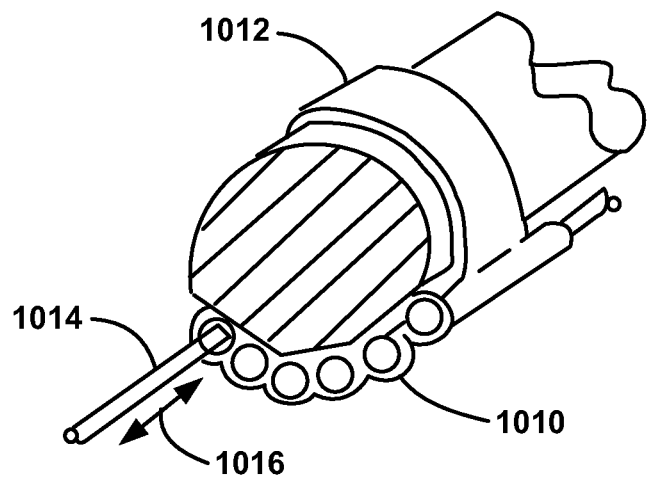
FIGS. 10A-C show an embodiment of the tubing management.
Figure 10B:
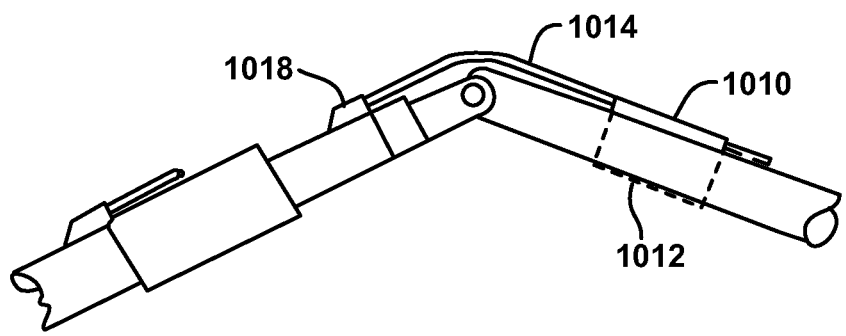
Figure 10C:
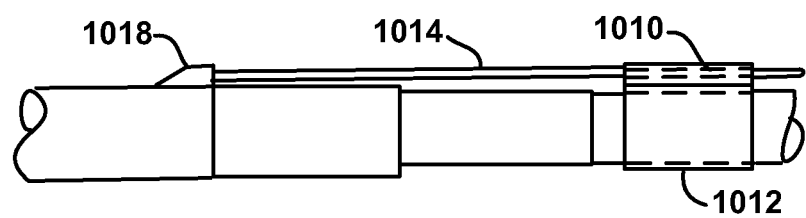

As shown in FIG. 4C, the front view of the extend module, the hydraulic tubing connecting the various modules to the control cylinders are located at one side of the slave cylinders. The hydraulic tubing runs alongside the cannula and connects to the inlet openings of the hydraulic portion of each module. In some embodiments of the invention, to keep the hydraulic tubing in place, a series of low friction guide tubes 1010 are attached to the cannula by an elastic strap 1012 (FIG. 10A). Each hydraulic tubing 1014 fits through one guide tubing and is free to move longitudinally, i.e., in the direction of the arrow 1016, within the guide tubing 1010. Thus, when the bend module bends, FIG. 10B, or when the extend module extends, FIG. 10C, the hydraulic tubing can move along the cannula and maintain the connection 1018 with the hydraulic inlets of each of the modules.

Figure 11A:
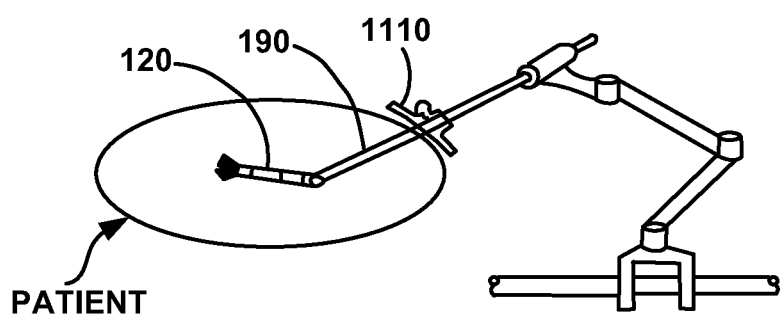
FIGS. 11A-B show an embodiment of the patient restraint.
Figure 11B:
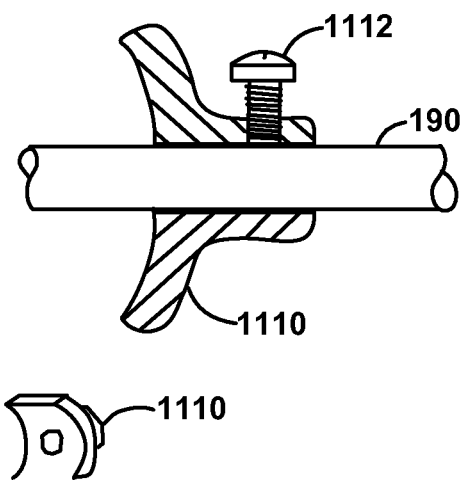

FIG. 11A shows an embodiment of the patient restraint, including a patient restraint 1110 with the distal end 120 of a cannula 190 directed towards the patient. In certain embodiments, the present invention features a restraint 1110 that can be attached to the cannula 190 using a thumb screw 1112 (FIG. 11B). The restraint 1110 sits adjacent to the patient's skin on the outside of the patient's body at the point of entry of the cannula 190. The restraint 1110 keeps the depth of the cannula 190 with respect to the body of the patient's body. If the patient makes any moves during the surgery, for example if the anesthesia begins to wear off and the patient jolts, the cannula moves with the patient. More importantly, the depth of the cannula inside the patient's body remains unchanged.

Figure 12A:
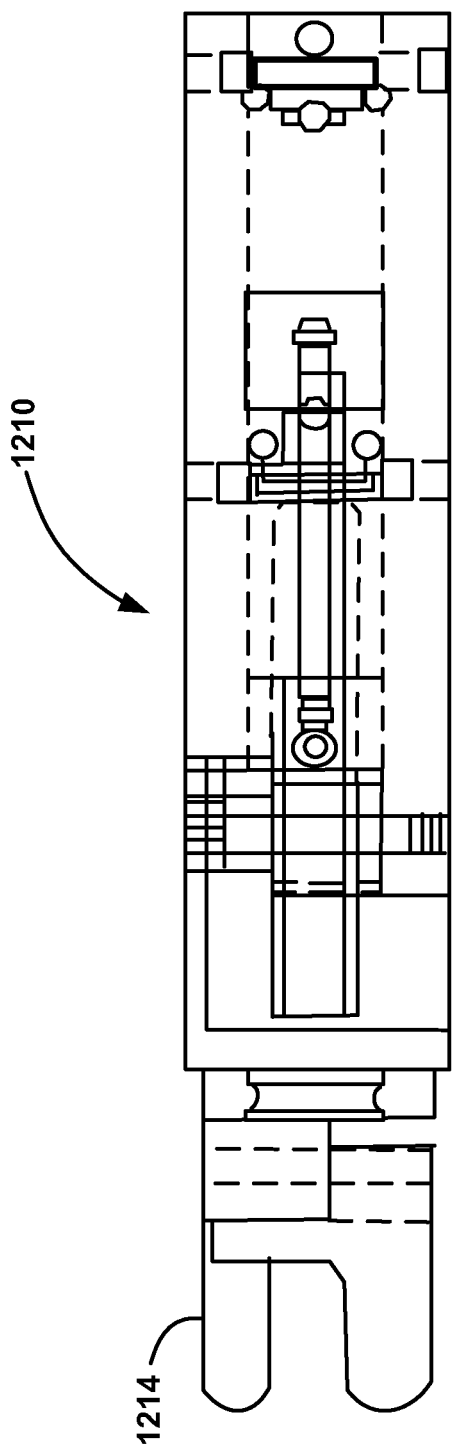
Figure 12B:
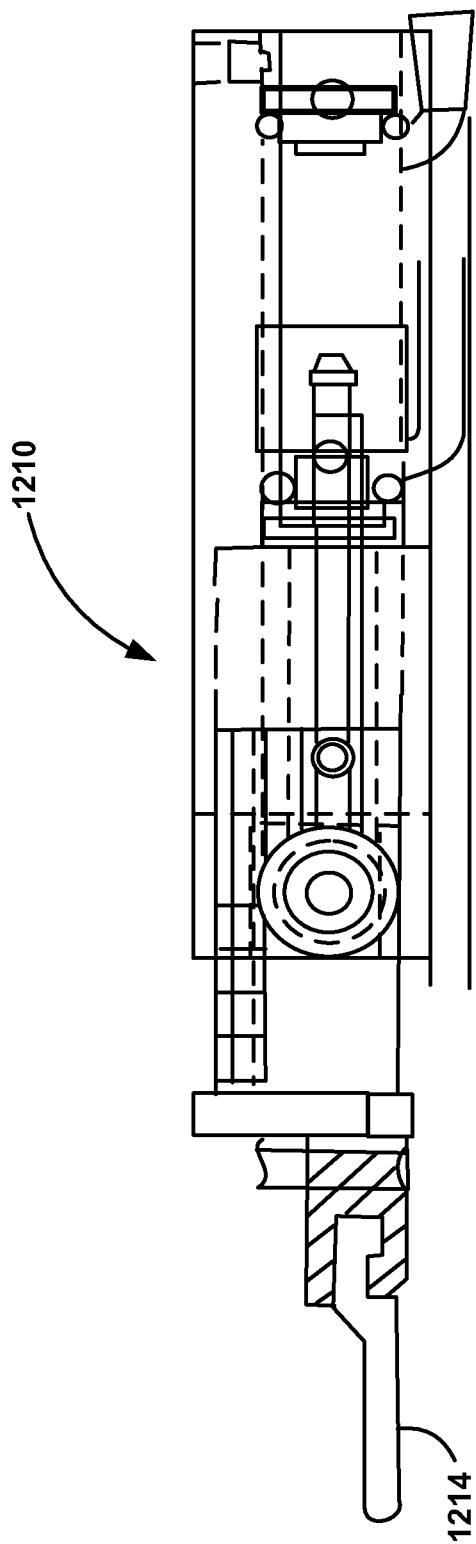

As part of their normal physiological function, certain organs in the body have continuous motion. For example, the heart beats, the lungs expand and contract as the patient breathes, and the gastrointestinal tract also undergoes contractile motion. When performing surgery, it is often necessary stabilize the part of the organ undergoing surgery so that additional injury to the organ does not occur and the organ can be worked on. Aspects of the invention also feature a tissue restraint module 1210 (FIGS. 12A-B) that can be inserted into the patient's body at or near the site where any other cannula has been inserted. The tissue restraint module 1210 features a bend module, as described above. Once inserted into the patient's body, the separable tynes 1214 can be brought dose to the tissue that is to be restrained. The bend module allows the tyne assembly to be bent with respect to the cannula, so that the tynes 1214 may be placed over the tissue. The tynes 1214 are separable.

Figure 12C:
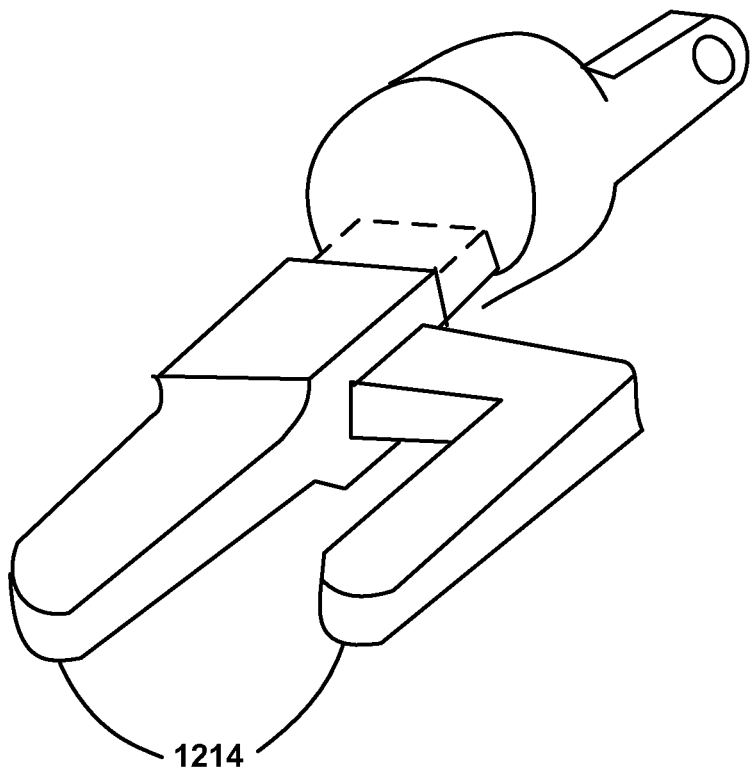
FIGS. 12C-E show various embodiments of the separable tynes of the tissue restraint modules.
Figure 12D:
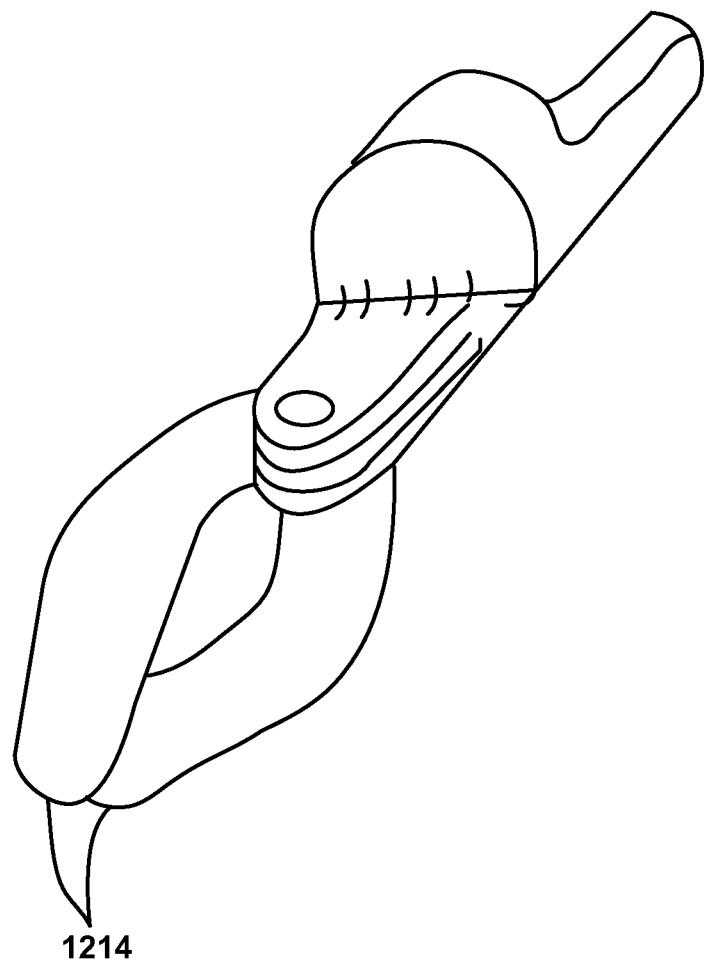
Figure 12E:
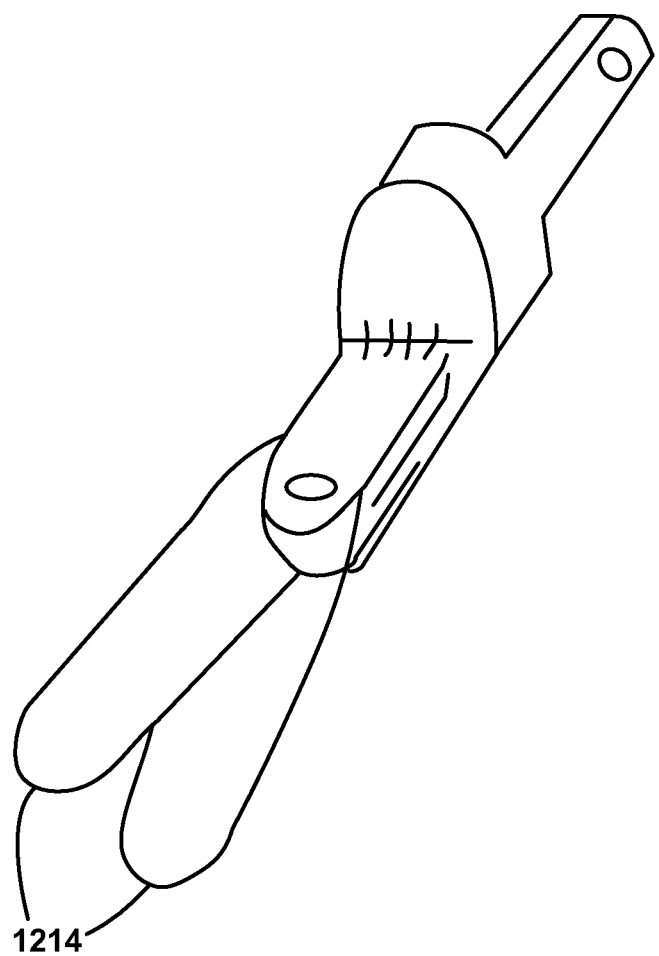

A number of different mechanisms for separating the tynes 1214 are shown in FIGS. 12C-E. In the embodiments shown, the tissue restraint module comprises two tynes 1214. The tynes 1214 are adapted to be separable. When inserting the module into the patient's body, the tynes 1214 are held together to reduce the width of the device. Inside the patient's body, the tynes 1214 can be separated. In the embodiment shown in FIG. 12C, one tyne 1214 is stationary, while the second tyne 1214 slides away from the first tyne 1214. In the embodiment shown in FIG. 120, both tynes 1214 move away from the center. Since the two tynes 1214 are bent inward, in their fully extended position the distal end of the two tynes 1214 would be parallel to each other. The embodiment shown in FIG. 12E functions similarly, except that the two tynes are not bent. In the fully extended position the two tynes 1214 form a "V" shaped opening. Other embodiments are also contemplated. For example, the tissue restraint module may comprise only one tyne. In certain embodiments, the single-tyne module may have a shape such as "∩", "⌐", or "⊤".

In certain embodiments, the tissue restraint module is held against a tissue or an organ during the surgical procedure. By doing so, in the space between the two tynes 1214, or a particular space created within a single tyne, a surface area of the tissue or organ becomes restrained, i.e., the local motion of the tissue or the organ is considerably reduced as compared with an unrestrained region of the tissue or the organ. The restraining of the tissue or the organ provides a relatively stable area on which the user can perform the surgical procedure.

In certain embodiments, the intermediate portion 190 of the cannula can be adapted to hold a number of different tools to be used during the operation. The cannula may be the cannula lending to the grasp module 710 at the distal end 120 of the device. During the operation, the user can retrieve a first tool from the cannula while within the patient's body and attach it to the grasp module 710. After using the first tool, the user can then return the first tool to the cannula, retrieve a second tool and attach it to the grasp module 710. Other tools may subsequently be used in a similar fashion.

The cannula 190 is held in place using a positioning arm 140 (see FIG. 1). The positioning arm 140 comprises at least one joint capable of being tightened or loosened using a release mechanism. The user can release the joint, move the positioning arm 140 to a desired location, and thereby reposition the cannula 190. In one embodiment, the invention provides for a one-hand-release mechanism. In this embodiment, the user can grasp the positioning arm 140 with one hand, and while holding the positioning arm 140, loosen the joint using the same hand, move the positioning arm 140 to a new location using the same hand, and then tighten the joint, again using the same hand. The one-hand-release mechanism allows the user to reposition the cannula using one hand, while manipulating the distal end 120 of the device using the control portion 110 with the other hand.

In using the devices of the present invention, it is often the case that the tools at the distal portion of the device are to move a short distance. This distance is small enough that it would become difficult for the user to move his hands or fingers for that short a distance. Therefore, a system is needed to convert a longer movement of the user's hands and fingers at the proximal end of the device to a short movement of the tools at the distal end of the device. This is accomplished by having the control cylinder and the slave cylinder be of different diameters. Of importance, is the relationship between the piston area and the shaft area when using cylinders of different diameters, as generally described below.

Figure 16A:
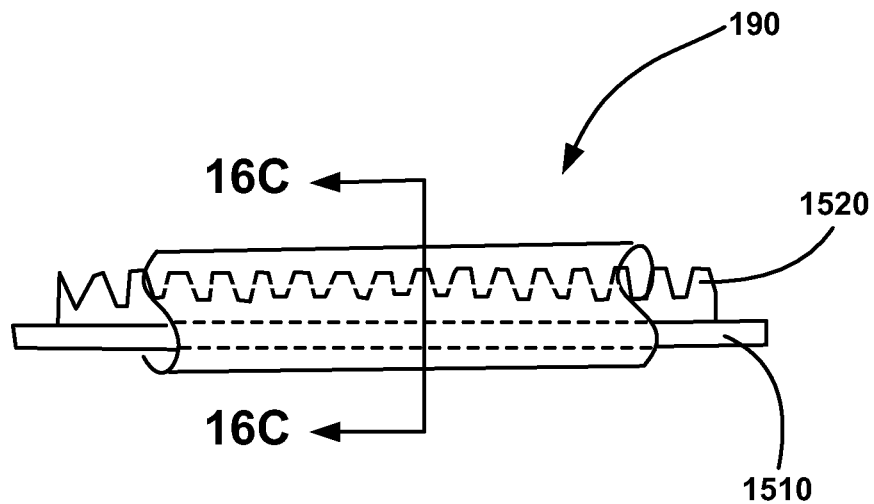
FIGS. 16A-C are side views showing the articulation mechanism of FIGS. 15A-B in greater detail.
Figure 16B:
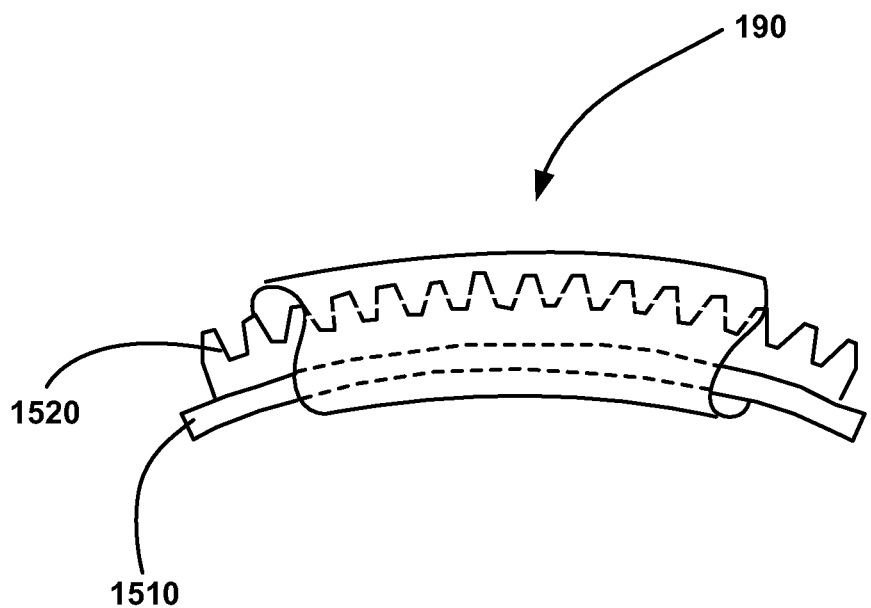
Figure 16C:
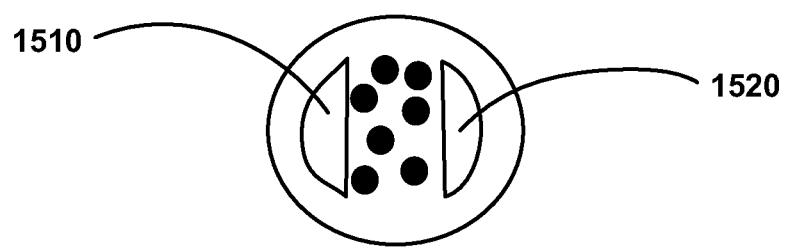

At least a portion of the intermediate portion 190 of the laparoscopic tool is an articulation portion. FIGS. 15A-B and 16A-C illustrate one embodiment of an articulation mechanism implemented in the articulation portion of the intermediate portion 190. A spring bar 1510 is embedded within the body of the outer sleeve. The spring bar may be made of any material, such as plastic or metal, that allows it to resiliently bend while exerting a reacting force against the bending. The spring bar 1510 acts to prevent the articulation portion from bending unless a force is exerted to cause it to bend. An opposite wall of the sleeve is lined with small pouches 1520. FIG. 16C illustrates the arrangement of the pouches 1520 and the spring bar 1510 in a cross-sectional view of the articulation portion. The pouches 1520 are densely placed along the length of the articulation portion. The pouches 1520 are connected to a reservoir of hydraulic liquid (not shown) by a series of orifices or valves in each pouch. When hydraulic fluid is supplied to the pouches 1520 through the orifices or valves, the pouches 1520 are filled with the hydraulic liquid. The filled pouches 1520 press against one another and force an expansion of the side of the articulation portion with the pouches 1520. This expansion causes the spring bar 1510 to bend, causing the articulation portion to bend, as shown in FIG. 16B.

Double Acting/Double Cylinder System

Figure 13:
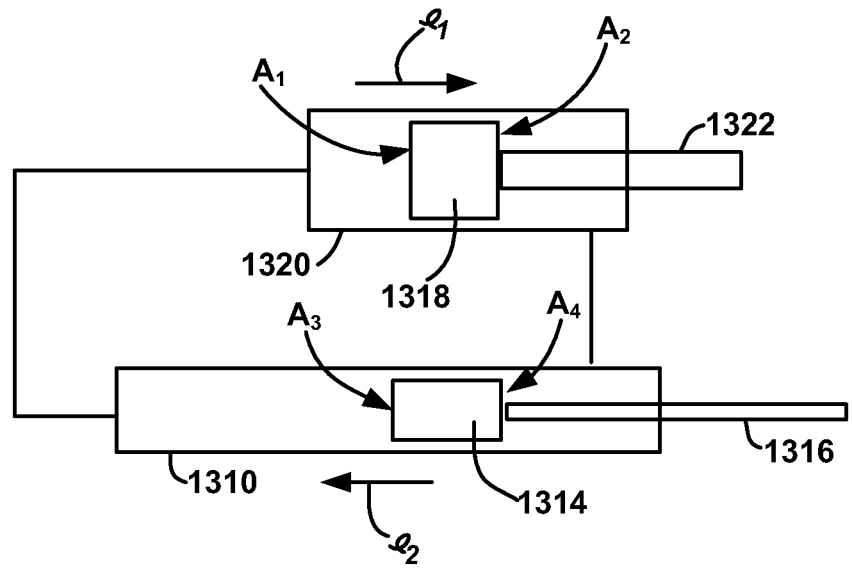
FIG. 13 shows the different cylinder diameters for changing the ratio of movement between the control cylinder and slave cylinder.

Another aspect of the present invention includes a double acting/double cylinder system. This system is depicted in FIG. 13. The system comprises a control cylinder 1320 and a slave cylinder 1310. The control cylinder comprises a piston 1318 and a shaft 1320 attached thereto. The piston 1318 is capable of moving within the control cylinder 1320. The piston divides the control cylinder into two cavities: a distal cavity, a wall of which is $A_1$, and a proximal cavity, a wall of which is $A_2$. The shaft 1322 passes through the proximal cavity. The piston 1318 prevents liquid communication between the distal cavity and the proximal cavity.

The slave cylinder comprises a piston 1314 and a shaft 1316 attached thereto. The piston 1314 is capable of moving within the slave cylinder 1310. The piston divides the slave cylinder into two cavities: a distal cavity, a wall of which is $A_3$, and a proximal cavity, a wall of which is $A_4$. The shaft 1316 passes through the proximal cavity. The piston 1314 prevents liquid communication between the distal cavity and the proximal cavity.

A control line provides hydraulic communication between the proximal cavity of the control cylinder and the proximal cavity of the slave cylinder. Another control line provides hydraulic communication between the distal cavity of the control cylinder and the proximal cavity of the slave cylinder. Thus, in the system, the two distal cavities are in hydraulic communication with each other, the two proximal cavities are in hydraulic communication with each other, but no proximal cavity is in hydraulic communication with any distal cavity.

If the control cylinder piston 1318 moves towards the distal end of the control cylinder 1320, hydraulic fluid is moved from the distal cavity of the control cylinder, through a control line, and into the distal cavity of the slave cylinder, thereby pushing the slave cylinder piston 1314 towards the proximal end of the slave cylinder 1310. The reverse may also happen. If the control cylinder piston 1318 moves towards the proximal end of the control cylinder 1320, hydraulic fluid is moved from the proximal cavity of the control cylinder, through a control line, and into the proximal cavity of the slave cylinder, thereby pushing the slave cylinder piston 1314 towards the distal end of the slave cylinder 1310. Further, while the control cylinder piston 1318 remains stationary, the salve cylinder piston 1314 also remains stationary.

In an embodiment, the double acting/double cylinder system of the invention comprises an overpressure reservoir. If the hydraulic pressure within the cylinders or the control lines exceeds a certain amount, some hydraulic fluid is transferred to the overpressure reservoir. The opening to the overpressure reservoir may comprise a pressure gauge device, which can become activated when the hydraulic pressure within a system surpasses a certain preset value. When the pressure gauge device is activated, the opening to the overpressure reservoir opens and hydraulic fluid can then enter the reservoir.

In another embodiment, the overpressure reservoir comprises an opening, which communicates with rest of the hydraulic circuits when it is placed in storage mode. When in use mode, the hydraulic fluid in the reservoir is completely cut off form the rest of the circuits. The purpose of the reservoir is to rehydrate the circuit when in storage mode.

The reservoir further comprises a spring mechanism at the side opposite to the opening. When the hydraulic pressure within the system surpasses the pressure applied by the spring mechanism, hydraulic fluid enters the reservoir from the system. Conversely, when the pressure within the system falls below the pressure applied by the spring mechanism, for example due to a leak in the system, hydraulic fluid enters the system from the reservoir. Thus, the reservoir may also function as a fluid replacement reservoir.

In certain embodiments, the flow of the hydraulic fluid inside the system will move very easily so that not enough resistance is afforded. In these situations, it is difficult for a user to control the movement of the cylinders with fine precision. Therefore, certain embodiments of the invention feature a narrowing at a point in the hydraulic tubing, the purpose of which is to create resistance. In some embodiments, the user can change the amount of narrowing, and therefore, the amount of resistance in the hydraulic tubing, FIG. 13 depicts the relationship between the control cylinder 1310 and the slave cylinder 1312. The control cylinder 1310 has a piston 1314 and a shaft 1316. The front of the piston 1314, i.e., the opposite face from where the shaft 1316 attaches to the piston 1314, has an area of $A_3$ and the back of the piston 1314, i.e., the face where the shaft 1316 attaches, has an area is $A_4$. Thus, $A_3$ is equal to $A_4$ plus the area of the shaft 1316. When the piston 1314 moves backwards a distance of $I_2$, the amount of hydraulic fluid displaced in front of the piston 1314 will have a volume of $A_3 I_2$. However, the volume of the hydraulic fluid displaced behind the piston 1314 will be $A_4 I_2$.

The slave cylinder 1312 also has a piston 1318 and a shaft 1320. The volumes of displaced hydraulic fluid in front of and behind the piston 1318 must be equal to the volume of displaced hydraulic fluid in front of and behind the piston 1314. In other words, $$A_1 I_1 = A_3 I_2$$

and $$A_2 I_1 = A_4 I_2$$

where $I_1$ is the distance traveled by the slave cylinder. Rearranging the equations results in $$I_2 = \frac{A_1 I_1}{A_3} = \frac{A_2 I_1}{A_4}$$

which result in the basic relationship between the various surface areas as $$\frac{A_1}{A_3} = \frac{A_2}{A_4}$$

It is readily understood by those of skill in the art that the above relationship will also hold true if the control cylinder and the slave cylinder are configured such that small movements by the user's hands and fingers results in longer movements at the distal end of the device. In other words, in FIG. 13, in one embodiment 1312 represents the slave cylinder and 1310 represents the control cylinder, whereas in another embodiment, 1312 represents the control cylinder and 1310 represents the slave cylinder.

Figure 14:
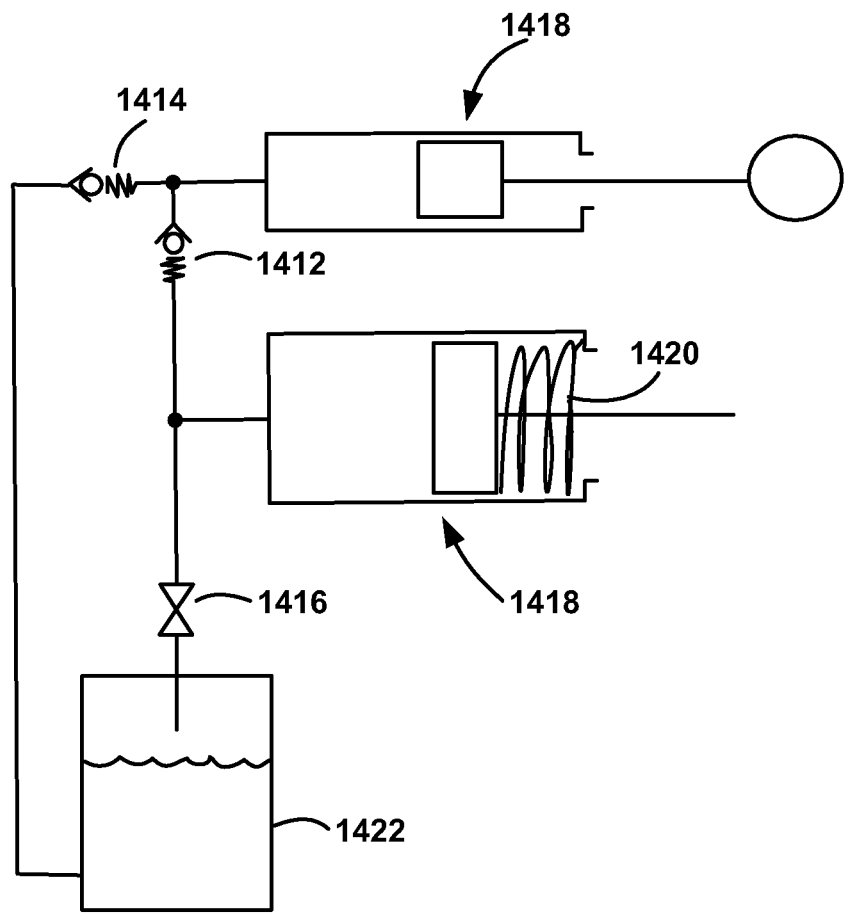
FIG. 14 shows an embodiment of the multiple stroke cylinder.
Figure 15A:
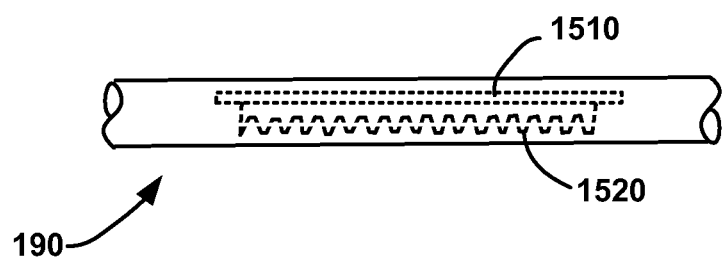
FIGS. 15A-B are side views showing the articulation mechanism of the present invention.
Figure 15B:
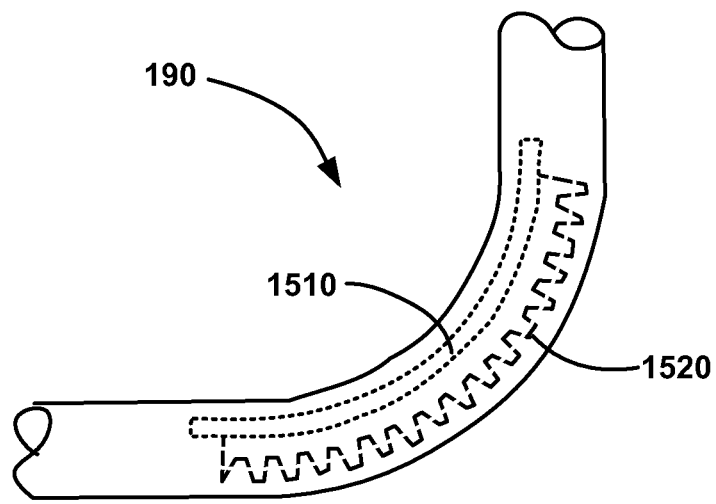

In certain embodiments, when it is desirable to have a long range of movement or very fine movement at the distal end of the device, a full range of movement at a slave cylinder at the distal end of the device may be affected by using multiple strokes of a control cylinder. In these embodiments, the present invention features a multiple stroke cylinder system (FIG. 14). A stroke of the control cylinder 1410 causes check valve 1414 to dose and check valve 1412 to open. Hydraulic fluid is then transferred from the control cylinder 1410 to the slave cylinder 1418. Returning the piston of the control cylinder 1410 to the original position, i.e., at the proximal end of the control cylinder, causes the check valve 1412 to dose and the check valve 1414 to open. Additional hydraulic fluid is then transferred from the reservoir 1422 to the control cylinder 1410. Another stroke of the control cylinder 1410 will then cause additional movement in the slave cylinder 1418.

The system is also equipped with a "dump" valve 1416. The dump valve 1416 may be activated by the user at anytime. When the dump valve 1416 is activated, hydraulic fluid is transferred from the slave cylinder 1418 back to the reservoir 1422. The dump valve 1416 has three modes: use; storage; and brake. When the dump valve 1416 is place in storage mode, the reservoir 1422 is connected to the rest of the circuit and will replenish the water in the circuit. In the "use" mode the reservoir 1422 is completely cut off from the rest of the circuit and only the master cylinder is connected to the slave cylinders. In the "brake" mode, the master and slave cylinders are completely cut off from each other. The reservoir 1422 is also cut off form the rest of the circuit in the "brake" mode.

In some embodiments, to aid the removal of the hydraulic fluid from the slave cylinder 1418 a spring mechanism 1420 is placed behind the piston of the slave cylinder. Those of skill in the art know of other mechanisms that can be used to return the piston of the slave cylinder to its original position.

In other embodiments, the system is so configured that the user can reverse the flow of the hydraulic fluid. Therefore by additional strokes of the control cylinder the user can remove hydraulic fluid from the slave cylinder 1418 and transfer it back to the reservoir 1422.

Figure 17:
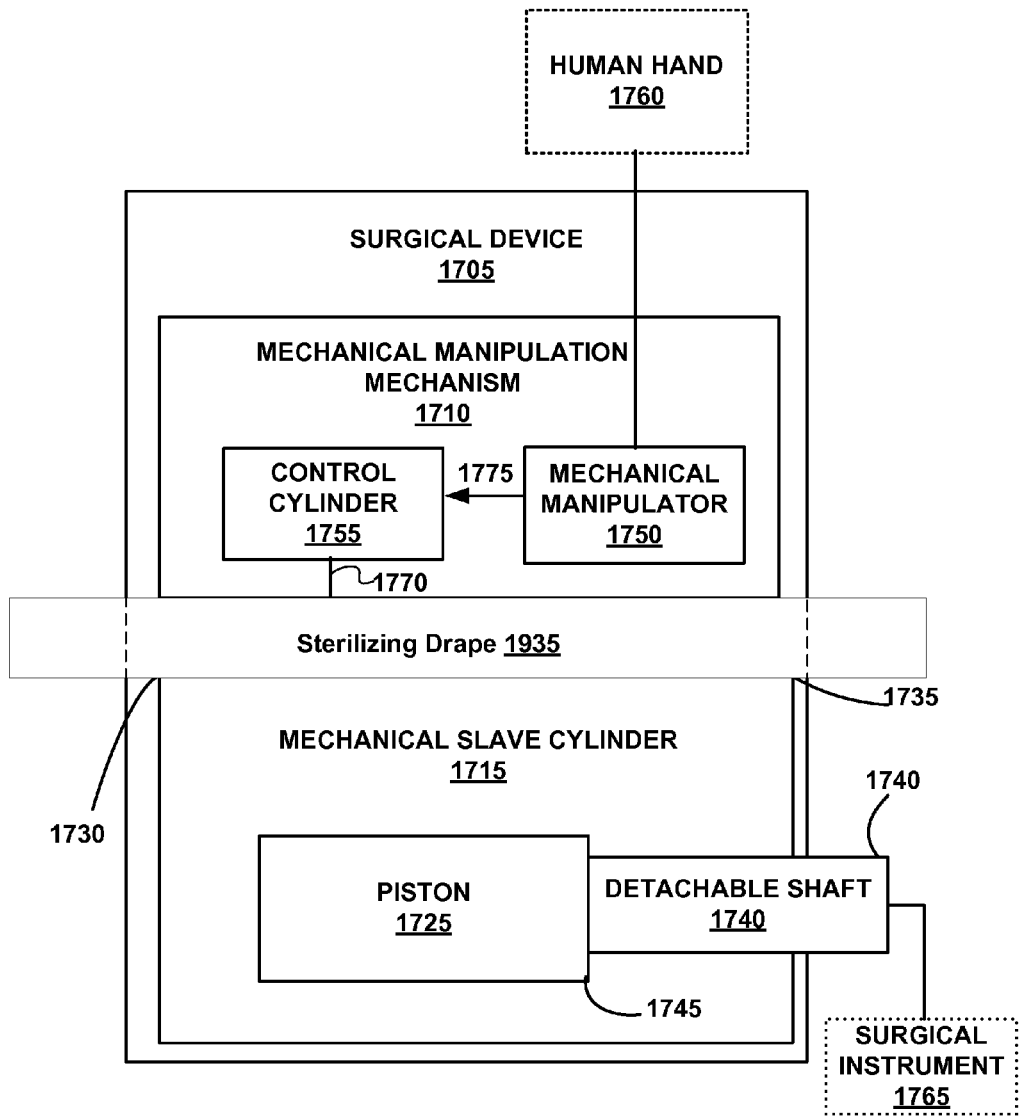
FIG. 17 is a block diagram of a surgical device, in accordance with embodiments of the present invention.

Referring now to FIG. 17, a block diagram of a surgical device 1705 is shown, in accordance with embodiments of the present invention. FIG. 17 shows a surgical device 1705 comprising at least one mechanical manipulation mechanism 1710 coupled with at least one mechanical slave cylinder 1715. For purposes of brevity and clarity, the reference to the mechanical manipulation mechanism 1710 and the mechanical slave cylinder 1715 will be in the singular. However, it is understood that, in accordance with embodiments of the present invention, there may be more than one mechanical manipulation mechanism 1710 and mechanical slave cylinder 1715, The mechanical manipulation mechanism 1710 is configured for transmitting a first set of control signals 1770. The mechanical slave cylinder 1775 is positioned at a distal end of the surgical device 1705 and is configured for receiving the first set of control signals 1770. The mechanical slave cylinder 1775 comprises a piston 1725 and a detachable shaft 1740. The piston 1725 is configured for responding to the first set of control signals 1770 by moving between a proximal end 1730 and a distal end 1735 of the mechanical slave cylinder 1715. The detachable shaft 1740 is configured for detachably coupling with a distal end 1745 of the piston 1725 and for moving with the piston 1725.

In one embodiment, the mechanical manipulation mechanism 1710 comprises at least one manipulator 1750 coupled with at least one control cylinder 1755. For purposes of brevity and clarity, the reference to the manipulator 1750 and the control cylinder 1755 will be in the singular. However, it is understood that, in accordance with embodiments of the present invention, there may be more than one manipulator 1750 and control cylinder 1755.

In one embodiment, the manipulator 1750 is configured for being controlled by a human hand 1760 and for actuating the control cylinder 1755 by mechanically transmitting a second set of control signals 1775 from the manipulator 1750 to the control cylinder 1755. The control cylinder 1755 is positioned at a proximal end of the surgical device 1705 and is configured for transmitting the first set of control signals 1770 to the mechanical slave cylinder 1715.

In one embodiment, the mechanical slave cylinder 1715 is in hydraulic communication with the control cylinder 1755 and is configured for responding to hydraulic control signals of the first set of control signals 1770 transmitted by the control cylinder 1755. In one embodiment, the first set of control signals 1770 are transmitted via a cable and pulley system.

In one embodiment, the detachable shaft 1740 is configured to be reusable within the surgical device 1705. In one embodiment, the detachable shaft 1740 is configured to be sterilized after detachment. In yet another embodiment, the distal end 1742 of the detachable shaft 1740 is configured for detachably coupling with a surgical instrument 1765. In one embodiment, the surgical instrument 1765 is part of the detachable shaft 1740. In another embodiment, the surgical instruction 1765 is a instrument separate from the detachable shaft 1740.

Furthermore, in one embodiment, the detachable shaft 1740 is disposable. For example, in one embodiment, the detachable shaft 1740 is disposed after its use within a single patient. By being disposable, this eliminates the potential for cross contamination of bodily fluids from patient to patient.

In embodiments of the present invention, the detachable shaft 1740 may be made of any material that is suitable for being coupled with the piston 1725, for a sterile environment, and for being coupled with a surgical instrument 1765 such that the surgical instrument 1765 is operable for its intended purpose. For example, the detachable shaft 1740 may be plastic. In yet another example, the detachable shaft 1740 may be metal. In one embodiment, the detachable shaft 1740 is composed of a combination of materials. For example, the detachable shaft 1740 may be part plastic, and/or made primarily of plastic, in addition to other materials. In another embodiment, the detachable shaft 1740 may be part and/or made primarily of metal, in addition to other materials.

In one embodiment, the detachable shaft 1740 is hallow. In another embodiment, the detachable shaft 1740 that is hallow is configured for performing at least, but not limited to, one of the following: suctioning, illuminating, transporting gasses, irrigating, and providing a pathway for wires therein. In one embodiment, these wires are electrical wires.

Figure 18:
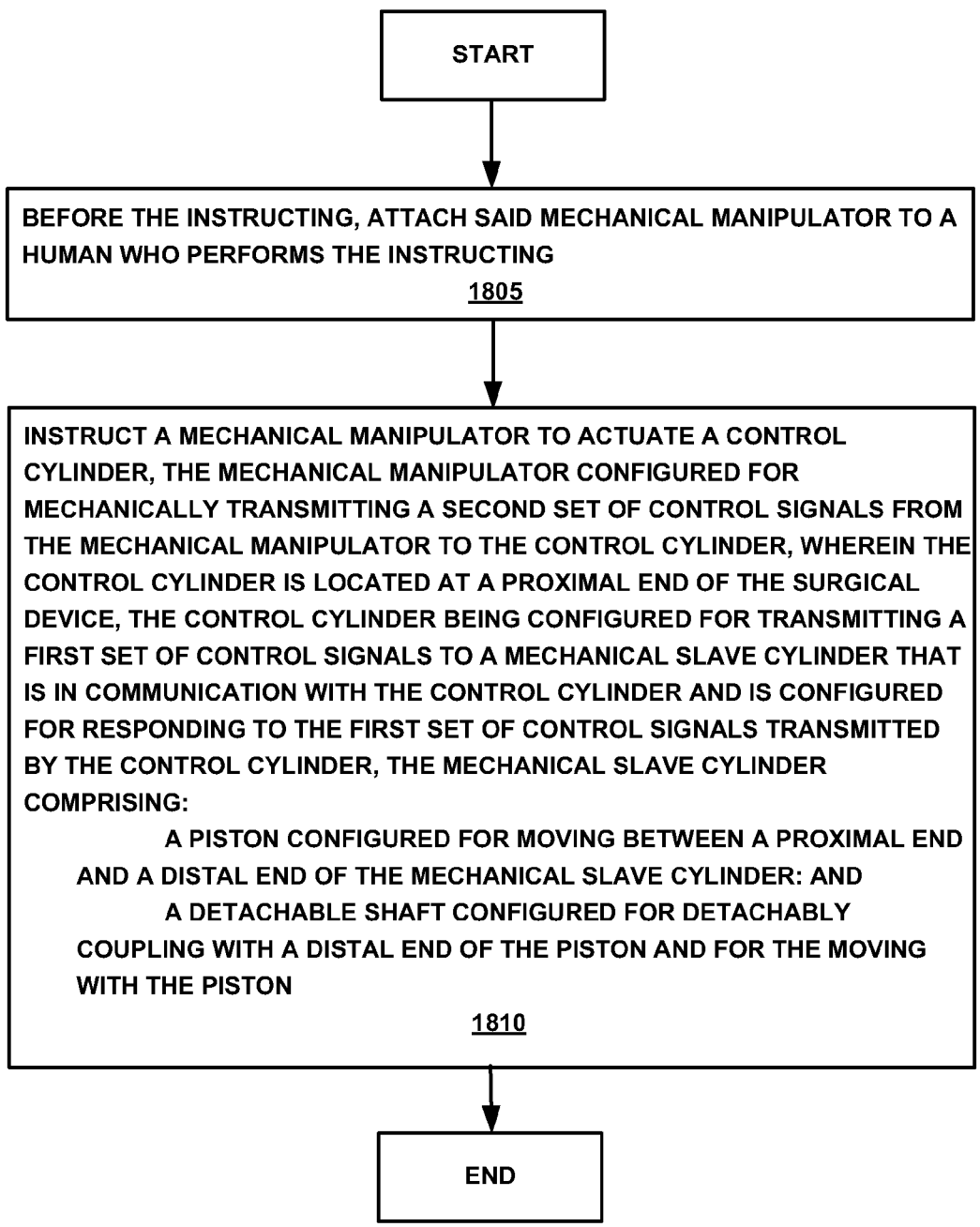
FIG. 18 is a flow diagram of a method for using a surgical device, in accordance with embodiments of the present invention.

Referring now to FIGS. 17 and 1800 of FIG. 18, a flow diagram of a method for using a surgical device 1705 is shown in accordance with embodiments of the present invention. Referring now to FIGS. 17 and 1810 of FIG. 18, a mechanical manipulator 1750 is instructed to actuate a control cylinder 1755. The mechanical manipulator 1750 is configured for mechanically transmitting a second set of control signals 1775 from the mechanical manipulator 1750 to the control cylinder 1755. The control cylinder 1755 is located at a proximal end of the surgical device 1705 and is configured for transmitting a first set of control signals 1770 to a mechanical slave cylinder 1715 that is in communication with the control cylinder 1755 and is configured for responding to the first set of control signals 1770 transmitted by the control cylinder 1755. The mechanical slave cylinder 1715 comprises a piston 1725 and a detachable shaft 1740. The piston 1725 is configured for moving between a proximal end 1730 and a distal end 1735 of the mechanical slave cylinder 1715. The detachable shaft 1740 is configured for detachably coupling with the distal end 1745 of the piston 1725 and for moving with the piston 1725.

In one embodiment, the instructing 1810 comprises one of more, but not limited to, of the following instructions: bending, rotating, pushing, pulling, changing to various degrees of lateral movement and changing to various degrees of vertical movement.

Referring now to FIGS. 17 and 1805 of FIG. 18, in one embodiment, before the instructing 1810, the mechanical manipulator 1750 is attached to a human who performs the instructing 1810. In another embodiment, the mechanical manipulator 1750 need not be attached to a human for the instructing 1810 to be performed or received by the control cylinder 1755. Wireless methods may also be used for transmitting such instructions. Additionally, wireless methods may be used in conjunction with the mechanical methods for transmission of the instructions.

Figure 19:
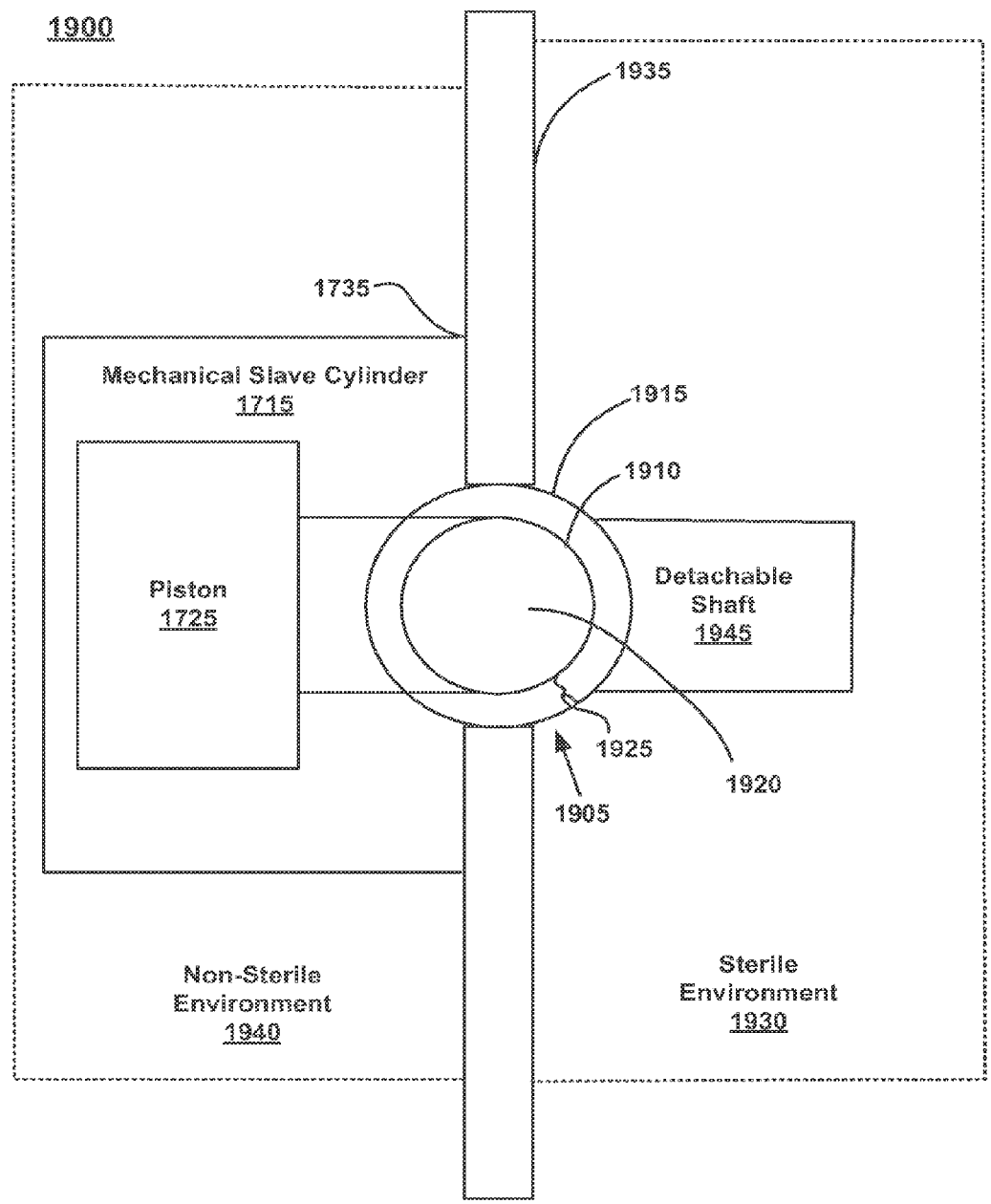
FIG. 19 is block diagram of an interface mechanism coupled with a mechanical slave cylinder, in accordance with embodiments of the present invention.

Referring now to FIGS. 17 and 1900 of FIG. 19, a block diagram of an interface mechanism coupled with a mechanical slave cylinder 1715 is shown, in accordance with embodiments of the present technology. In one embodiment, an interface mechanism 1905 sealingly couples the distal end 1735 of the mechanical slave cylinder 1715 with a draping material 1935. By sealingly couples, it is meant that matter does not pass from one side of the draping material 1935 to the other side, through the area in which the interface mechanism 1905 couples with the distal end 1735 of the mechanical slave cylinder 1715 and the draping material 1935.

The draping material 1935 is configured for isolating a portion of the surgical device 1705 within a sterile environment 1930. The portion of the surgical device 1705 that is isolated within the sterile environment 1930 is the portion of the shaft 1945 that moves through the ring 1925 and is within the sterile environment 1930 side of the draping material 1935. The sterile environment 1930 refers to an environment intended to be maintained in a state that only contains the living organic material desired by the operator of the surgical device 1705.

On one side of the draping material 1935 lies the surgical device 1705, in the non-sterile environment 1940. On the other side of the draping material 1935 lies the sterile environment 1930. Additionally, a patient may also be within the sterile environment 1930, upon which the surgical device 1705 is being remotely controlled by a human hand 1760 to perform a surgery.

In one embodiment, the interface mechanism 1905 comprises a ring 1925 defining an opening 1920 through the draping material 1935 and configured for receiving the shaft 1945 there through as the shaft 1945 moves with the piston 1725. In one embodiment, the ring 1925 comprises: an inner portion 1910, and an outer portion 1915. The inner portion 1910 is sealingly coupled with a portion of the distal end 1735 of the mechanical slave cylinder 1715. In one embodiment, the outer portion 1915 is coupled with the inner portion 1910 and is sealingly coupled with the draping material 1935.

In one embodiment, the outer portion 1915 and the inner portion 1910 are two separate components that are coupled with each other. In another embodiment, the outer portion 1915 and the inner portion 1910 are part of a single component. In other words, the ring 1925 may be made up of one or more components.

In one embodiment, the interface mechanism 1905 is plastic. In another embodiment, the interface mechanism 1905 is metal. In yet another embodiment, the interface mechanism 1905 is made of a material selected from at least one of the following materials: metals, plastics and ceramics. Thus, the interface mechanism 1905, in one embodiment, is a combination of materials, In one embodiment, the ring 1925 of the interface mechanism 1905 is of a non-circular shape. For example, the ring 1925 may be round, oval, square, diamond shape, etc. Thus, in one embodiment, the shaft 1945 also may be of a non-cylindrical shape. For example, but not limited to, the shaft 1945 may be rectangular. Furthermore, in one embodiment, the shaft 1945 may be detachable, as explained herein. However, whatever the shape of the ring 1925 and the shaft 1945, both the ring 1925 and the shaft 1945 much be compatible, thereby enabling the shaft 1945 to move through the ring 1925, in a manner in which liquid does not flow from one side of the draping material 1935 to the other side.

Furthermore, it should be noted that the interface mechanism 1905 is designed in such a way as to maintain the sterility of the sterile environment 1930. Thus, as described herein, a liquid or other contaminants may not flow from one side of the draping material 1935 to the other side, through the interface mechanism 1905. In another embodiment, the interface mechanism 1905 is waterproof.

Figure 20:
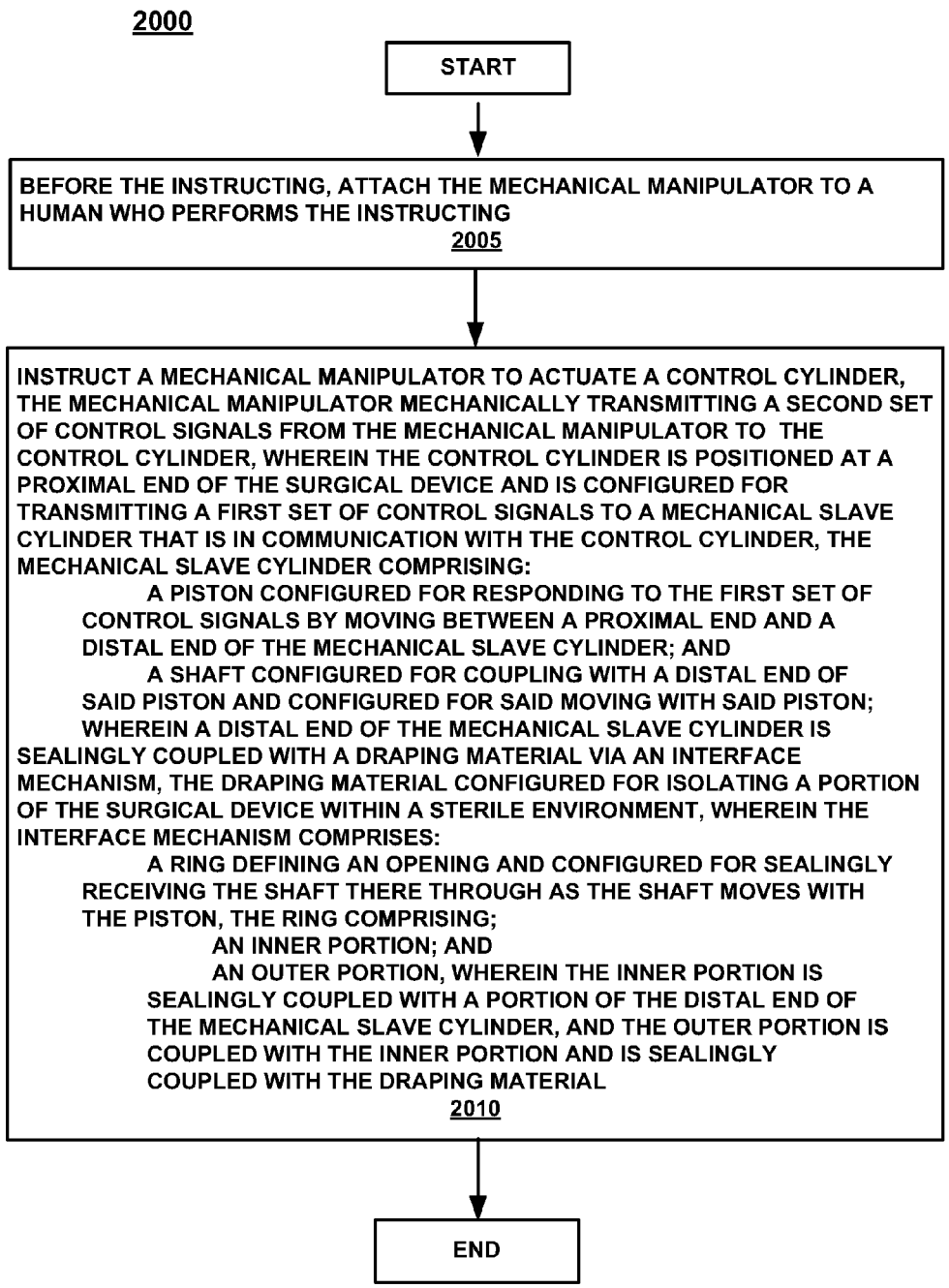
FIG. 20 is a flow diagram of a method for using a surgical device, in accordance with embodiments of the present invention.

Referring now to FIGS. 19 and 2000 of FIG. 20, a flow diagram of a method for using a surgical device is shown in accordance with embodiments of the present invention. Referring now to 1910, a mechanical manipulator 1750 is instructed to actuate a control cylinder 1755, the mechanical manipulator 1750 mechanically transmitting a second set of control signals 1775 from the mechanical manipulator 1750 to the control cylinder 1755, wherein the control cylinder 1755 is positioned at a proximal end of the surgical device 1705 and is configured for transmitting a first set of control signals 1770 to a mechanical slave cylinder 1715 that is in communication with the control cylinder 1755.

Furthermore, in one embodiment, the interface mechanism 1905 is reusable. For example, the interface mechanism 1905 is detachable from the sterile drape 1935. In one embodiment, after being detached, the interface mechanism 1935 may be sterilized. In another embodiment, the interface mechanism 1935 is reattached to the same sterile drape that was used before, or to different new sterile drape. In another embodiment, the interface mechanism 1905 is disposable.

The mechanical slave cylinder 1715 comprises a piston 1725 and a shaft 1945. The piston 1725 is configured for responding to the first set of control signals 1770 by moving between a proximal end 1730 and a distal end 1735 of the mechanical slave cylinder 1715. The shaft 1945 is configured for coupling with a distal end 1745 of the piston 1725 and is configured for moving with the piston 1725. Further, the distal end 1735 of the mechanical slave cylinder 1715 is sealingly coupled with a draping material 1935 via an interface mechanism 1905. The draping material 1935 is configured for isolating a portion of the surgical device 1705 within a sterile environment 1930.

The interface mechanism 1905 comprises a ring 1925. The ring 1925 defines an opening 1920 and is configured for sealingly receiving the shaft 1945 there through as the shaft 1945 moves with the piston 1725. The ring 1925 comprises an inner portion 1910 and an outer portion 1915. The inner portion 1910 is sealingly coupled with a portion of the distal end 1735 of the mechanical slave cylinder 1715. The outer portion 1915 is coupled with the inner portion 1910 and is sealingly coupled with the draping material 1935.

In one embodiment, the instructing 1910 comprises one or more, but not limited to, the following instructions: bending; rotating; pushing; pulling; changing to various degrees of lateral movement; and changing to various degrees of vertical movement. In response to these instructions, the shaft 1945 at least performs the following: bends, rotates, extends forward, extends backward, extends in a lateral direction, and extends in a vertical direction, respectively.

Thus, an operator, such as a surgeon, of the surgical device 1705 uses his hand 1760 to remotely control the surgical device 1705. The surgeon uses a manipulator 1750, such as finger loops, to give surgical instructions to the surgical device 1705. These instructions are translated into control signals (second set of control signals 1775), hydraulic or mechanical, that are sent to the control cylinder 1755. The control cylinder 1755 then sends control signals (first set of control signals 1770) to a mechanical slave cylinder 1715 that is attached to the shaft 1945. The shaft 1945 itself is coupled with a surgical instrument 1765 that moves within the patient. The instructions may ultimately guide the piston 1725 to move back and forth, while also guiding the surgical instrument 1765 to bend, grasp, turn, etc. within the patient.

Sterile Drape Having Multiple Drape Interface Mechanisms

Figure 21:
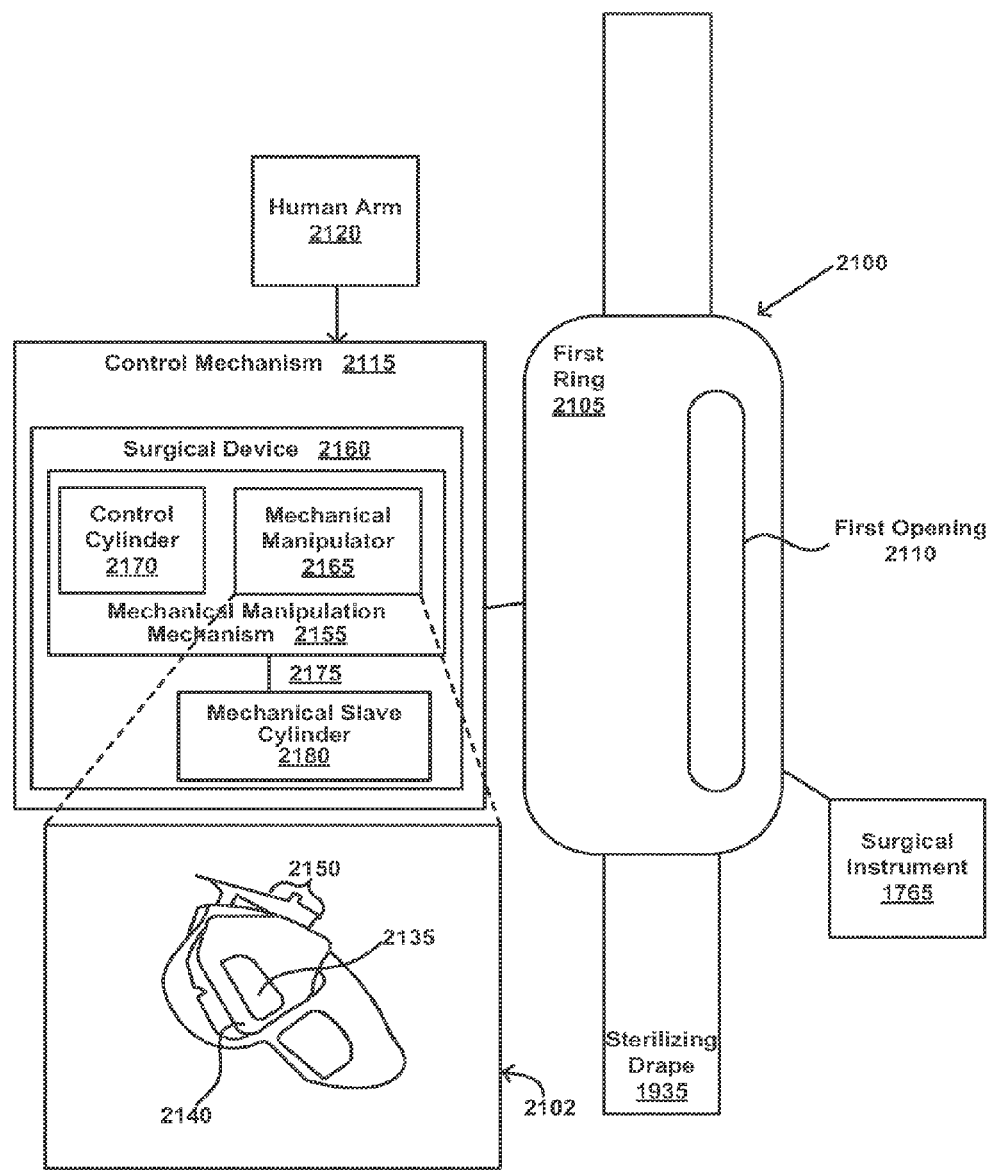
FIG. 21 is a block diagram of sterile drape having a drape/handle mechanism, in accordance with embodiments of the present invention.

Referring now to FIG. 21, a sterile drape 1935 configured for isolating a portion of a surgical device within a sterile environment is shown in accordance with embodiments of the present technology. In one embodiment, and referring to FIGS. 17, 19 and 21, a sterile drape 1935 that is configured for isolating a portion of a surgical device within a sterile environment comprises a plurality of drape interface mechanisms. The plurality of drape interface mechanisms comprises at least one drape/handle interface mechanism 2100 and at least one drape/shaft interface mechanism 1905 (also referred to herein as the "interface mechanism 1905"). While embodiments of the present technology provide for a possibility of a plurality of drape/handle interface mechanisms 2100 and a plurality of drape/shaft interface mechanisms 1905, for purposes of brevity and clarity, the drape/handle interface mechanism 2100 and the drape/shaft interface mechanism 1905 will be referred to herein in the singular.

In one embodiment, a drape/handle mechanism 2100 comprises a first ring 2105 defining a first opening 2100 through a sterile drape 1935. The drape/handle interface mechanism 2100 is configured for coupling with a control mechanism 2115. In one embodiment, the control mechanism comprises a surgical device 2160 for controlling a surgical instrument 1765.

In one embodiment and referring still to FIGS. 17, 19 and 21, the surgical device 2160 comprises a mechanical manipulation mechanism 2155 (alternatively referred herein as a second mechanical manipulation mechanism), a mechanical slave cylinder 2180 (alternatively referred herein as a second mechanical slave cylinder) and a connector 2175 (alternatively referred herein as a second connector).

In one embodiment, the mechanical manipulation mechanism 2180 is configured for receiving motion inputs in a plurality of degrees of freedom from a human arm 2120 and translating the motion inputs into a first set of control signals for controlling the motion of the surgical instrument 1765. In one embodiment, the mechanical manipulation mechanism 2155 comprises a mechanical manipulator 2165 and a control cylinder 2170.

In one embodiment, the mechanical manipulator 2165 comprises a user moveable bi-directional trigger 2140 configured for receiving a motion input of the motion inputs, a finger loop 2135 disposed within the trigger 2140 and configured for facilitating a user input of squeezing the trigger 2140 in a first direction. Further,in one embodiment, the mechanical manipulator 2165 includes a flange 2150 coupled to the trigger 2140 and configured for facilitating a user input of pushing the trigger 2140 in a second direction, the second direction being opposite of the first direction.

In one embodiment, the surgical device 2160 further comprises a mechanical slave cylinder 2180 coupled between the control cylinder 2170 and the surgical instrument 1765. The mechanical slave cylinder 2180 is configured for moving the surgical instrument 2160 in response to the first set of control signals. Moreover, in one embodiment, the surgical device 2160 includes a connector 2175 operatively coupled with the control mechanism 2115 and the mechanical slave cylinder 2180. The control cylinder 2170 is configured for causing the mechanical slave cylinder 2180 to move the surgical instrument 1765 by transmitting force applied by a human (for example, a human arm 2120) to the control mechanism 2115 through the connector 1770.

Referring still to FIGS. 17, 19 and 21, in one embodiment, the drape/shaft interface mechanism 1905 comprises a second ring 1925 defining a second opening 1920 through the sterile drape 1935. The drape/shaft interface mechanism 1905 is configured for sealingly receiving a shaft, for example but not limited to, detachable shaft 1945, there through as the shaft 1945 moves with a piston 1725 and is detachably coupled with the piston 1725.

In one embodiment, the piston 1725 is configured for responding to a first set of control signals sent by a first mechanical manipulation mechanism 1710 via a first connector 1770 by moving between a proximal end 1730 and a distal end 1735 of the mechanical slave cylinder 1715.

In one embodiment, the detachable shaft 1905 is configured to be sterilized after detachment. In yet another embodiment, the detachable shaft is configured to be reusable within the surgical device 1705. Furthermore, in one embodiment, the sterile drape 1935 is reusable.

In one embodiment, the first set and the second set of control signals are the same. In other words, the drape/handle interface mechanism 2100 is coupled with a control mechanism 2115 that is receiving control signals input from a human arm 2120 at the same time as the drape/shaft interface mechanism 1905 is sealingly receiving a detachable shaft 1945 there through as a result of the same control signals that are input through the same control mechanism 2115. Thus, the human arm is creating the input causing a surgical instrument 1765 to be moved as a result of a user moveable bi-directional trigger 2140 of the trigger grip control handle 2102 being manipulated, thereby manipulating the mechanical slave cylinder 2180 whose detachable shaft 1740 moves through the opening 1920 in ring 1925.

In one embodiment, the drape/handle interface mechanism 2100 and the drape/shaft interface mechanism 1905 are positioned on the same side of the sterile drape 1935.

In yet another embodiment, the connector 1770 operatively couples the mechanical manipulation mechanism 1710 with the mechanical slave cylinder 1715 through the drape/shaft interface mechanism 1905. Additionally, the connector 2175 operatively couples the mechanical manipulation mechanism 2155 and the mechanical slave cylinder 2180 through the drape/handle interface mechanism 2100. In other words, the connectors 1770 and 2175 go through the drape/handle and drape/shaft interfaces, 2100 and 1905 instead of around the sterile drape 1935.

In one embodiment, the connector 1770 operatively couples the mechanical manipulation mechanism 1710 with the mechanical slave cylinder 1715 by traveling around the sterile drape 1935. The connector 2175 operatively couples the mechanical manipulation mechanism 2155 with the slave cylinder 2180 by traveling around the sterile drape 1935. In other words, the connectors 1770 and 2175 go around the sterile drape 1935, and not through the drape/handle and drape/shaft interfaces 2100 and 1905, respectively, or through the sterile drape 1935.

In one embodiment, at least one of the drape/handle interface mechanism 2100 and the drape/shaft interface mechanism 1905 of the surgical device are plastic. In another embodiment, at least one of the drape/handle interface mechanism 2100 and the drape/shaft interface mechanism 1905 are metal. In one embodiment, at least one of said drape/handle interface mechanism and said drape/shaft interface mechanism comprises at least one of the following materials: metals, plastics and ceramics. In yet another embodiment, at least one of the drape/handle interface mechanism 2100 and the drape/shaft interface mechanism 1905 provides a water tight seal.

In one embodiment, the connectors 1770 and 2175 comprise a hydraulic system. In one embodiment, this hydraulic system comprises a closed-loop hydraulic system. In one embodiment the connectors 1770 and 2175 comprise a push-pull cable system. In another embodiment, the connectors 1770 and 2175 comprise a cable and pulley system. In yet another embodiment, the connectors 1770 and 2175 include more than one of a hydraulic system, a push-pull system, and a cable and pulley system.

It should be appreciated that the connectors 1770 and 2175 do not have to both be of the same system. For example, connector 1770 may comprise a hydraulic system,while connector 2175 comprises a cable and pulley system. Furthermore, there may be more than one connector coupled with one or more components of the surgical device and surgical system described herein.

Referring still to FIGS. 17, 19 and 21, a surgical system may be described thereby, in accordance with embodiments of the present technology. The surgical system comprises a surgical device that itself comprises: a mechanical manipulation mechanism 1710, at least one mechanical slave cylinder 1715, a connector 1770, at least one drape/handle interface mechanism 2100 and at least one drape/shaft interface mechanism 1905.

In one embodiment, the mechanical manipulation mechanism 1710 is configured for transmitting a first set of control signals. In one embodiment, the mechanical slave cylinder 1715 is coupled with the mechanical manipulation mechanism 1710 and positioned at a distal end 1735 of the surgical device 1705. The at least one mechanical slave cylinder 1715 is configured for receiving a first set of control signals. In one embodiment, the at least one mechanical slave cylinder 1715 includes a piston 1725 that is configured for responding to the first set of control signals by moving between a proximal end 1730 and a distal end 1735 of the mechanical slave cylinder 1715, and a shaft (in this case, a detachable shaft 1740) that is configured for detachably coupling with a distal end 170 of the piston 1725 and configured for moving with the piston 1725.

In one embodiment, the connector 1770 operatively couples with the mechanical manipulation mechanism 1720. The mechanical manipulation mechanism 1720 is configured for causing the mechanical slave cylinder 1715 to move the surgical instrument 1765 by transmitting a force applied by a human, such as a human hand 1760, to the surgical device 1705 through the connector 1770.

In one embodiment, the surgical device of the surgical system comprises at least one drape/handle interface mechanism 2100 comprising a ring 2105 defining an opening 2110 through a sterile drape 1935. The at least one drape/handle interface mechanism 2100 is configured for coupling with a control mechanism 2115, wherein the control mechanism 2115 comprises the surgical system.

In one embodiment, the mechanical manipulation mechanism 2155 is configured for receiving motion inputs in a plurality of degrees of freedom from the human arm (such as the human hand 1760) and translating these motion inputs into the set of control signals for controlling the motion of the surgical instrument 1765. In one embodiment, the mechanical manipulation mechanism 1710 comprises a mechanical manipulator 1750 and a control cylinder 1755. The mechanical manipulator 2165 includes a user moveable bi-directional trigger 2140 configured for receiving a motion input of the motion inputs, a finger loop 2135 disposed within the trigger 2140 and configured for facilitating a user input of squeezing the trigger 2140 in a first direction. Further, in one embodiment the mechanical manipulator 2165 includes a flange 2150 coupled to the trigger 2140 and configured for facilitating a user input of pushing the trigger 2140 in a second direction, the second direction being the opposite of the first direction. Additionally, the mechanical slave cylinder 2180 is coupled between the control cylinder 2170 and the surgical instrument 1765, the mechanical slave cylinder 2180 being configured for moving the surgical instrument 1765 in response to the first set of control signals.

Conclusion

Thus, those of skill in the art will appreciate that the devices described herein provide a relatively easy and economical instrument to perform minimally invasive surgery.

One skilled in the art will appreciate that these devices are and may be adapted to carry out the objects and obtain the ends and advantages mentioned, as well as those inherent therein. The methods, procedures, and devices described herein are presently representative of embodiments and are exemplary and are not intended as limitations on the scope of the invention. Changes therein and other uses will occur to those skilled in the art which are encompassed within the spirit of the invention and are defined by the scope of the disclosure.

It will be apparent to one skilled in the art that varying substitutions and modifications may be made to the invention disclosed herein without departing from the scope and spirit of the invention.

Those skilled in the art recognize that the aspects and embodiments of the invention set forth herein may be practiced separate from each other or in conjunction with each other. Therefore, combinations of separate embodiments are within the scope of the invention as disclosed herein.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising" "consisting essentially of" and "consisting of" may be replaced with either of the other two terms. The terms and expressions which have been employed are used as terms of description and not of limitation, and there is no intention that in the use of such terms and expressions indicates the exclusion of equivalents of the features shown and described or portions thereof. It is recognized that various modifications are possible within the scope of the invention disclosed. Thus, it should be understood that although the present invention has been specifically disclosed by embodiments and optional features, modification and variation of the concepts herein disclosed may be resorted to by those skilled in the art, and that such modifications and variations are considered to be within the scope of this invention as defined by the disclosure.

The invention claimed is:

1. A sterile drape configured for isolating a portion of a surgical device within a sterile environment, said sterile drape comprising:
    a plurality of drape interface mechanisms comprising:
        at least one drape/handle interface mechanism comprising a first ring defining a first opening through a sterile drape, said at least one drape/handle interface mechanism configured for coupling with a control mechanism, said control mechanism comprising a handle for controlling a surgical instrument; and
        at least one drape/shaft interface mechanism comprising a second ring defining a second opening through said sterile drape, said at least one drape/shaft interface mechanism configured for sealingly receiving a shaft there through as said shaft moves with a piston and is detachably coupled with said piston, wherein said piston is configured for responding to a first set of control signals sent by a first mechanical manipulation mechanism of a surgical device via a first connector by moving between a proximal end and a distal end of a first mechanical slave cylinder, and wherein said surgical device comprises:
        a second mechanical manipulation mechanism configured for receiving motion inputs in a plurality of degrees of freedom and translating said motion inputs into a second set of control signals for controlling motion of said surgical instrument, said second mechanical manipulation mechanism comprising a mechanical manipulator and a control cylinder, said mechanical manipulator comprising:
        a user moveable bi-directional trigger configured for receiving a motion input of said motion inputs;
        a finger loop disposed within said trigger and configured for facilitating a user input of squeezing said trigger in a first direction;
    and
        a flange coupled to said trigger and configured for facilitating a user input of pushing said trigger in a second direction, said second direction being opposite of said first direction;
        a second mechanical slave cylinder coupled between said control cylinder and said surgical instrument, said second mechanical slave cylinder configured for moving said surgical instrument in response to said first set of control signals; and
        a second connector operatively coupled with said control mechanism and said second mechanical slave cylinder, wherein said control cylinder is configured for causing said second mechanical slave cylinder to move said instrument by transmitting force applied to said control mechanism through said second connector, wherein said first connector and said second connector comprise a hydraulic system and said hydraulic system comprises a closed-loop hydraulic system,
    wherein said first connector operatively couples said first mechanical manipulation mechanism with said first mechanical slave cylinder through said at least one drape/shaft interface mechanism and said second connector operatively couples said second mechanical manipulation mechanism and said second mechanical slave cylinder through said at least one drape/handle interface mechanism.

2. The sterile drape of claim 1, wherein said shaft is configured to be reusable within said surgical device after being detached.

3. The sterile drape of claim 1, wherein said sterile drape is reusable.

4. The sterile drape of claim 1, wherein at least one of said drape/handle interface mechanism and said drape/shaft interface mechanism comprises at least one of the following materials: metals, plastics and ceramics.

5. The sterile drape of claim 1, wherein at least one of said drape/handle interface mechanism and said drape/shaft interface mechanism provide a water tight seal.

6. The sterile drape of claim 1, wherein said first connector operatively couples said first mechanical manipulation mechanism with said first mechanical slave cylinder around said sterile drape and said second connector operatively couples said second mechanical manipulation mechanism with said second mechanical slave cylinder around said sterile drape.

7. The sterile drape of claim 1, wherein said shaft is configured to be sterilized after detachment.

8. The sterile drape of claim 1, wherein said shaft is configured to be disposable.

9. The sterile drape of claim 1, wherein said first and second connectors comprise a push-pull cable system.

10. The sterile drape of claim 1, wherein said first and second connectors comprise a cable and pulley system.

11. The sterile drape of claim 1, wherein said first and second connectors include more than one of a hydraulic system, a push-pull cable system, and a cable and pulley system.

12. A surgical system, comprising:
    a surgical device comprising:
    a first mechanical manipulation mechanism configured for transmitting a first set of control signals;
    at least one mechanical slave cylinder coupled with said first mechanical manipulation mechanism and positioned at a distal end of said surgical device, said at least one mechanical slave cylinder configured for receiving said first set of control signals, wherein said at least one mechanical slave cylinder comprises:
    a piston configured for responding to said first set of control signals by moving between a proximal end and a distal end of said mechanical slave cylinder; and
    a shaft configured for detachably coupling with a distal end of said piston and configured for said moving with said piston;
    a first connector operatively coupled with said first mechanical manipulation mechanism and said mechanical slave cylinder, wherein said first mechanical manipulation mechanism is configured for causing said mechanical slave cylinder to move a surgical instrument by transmitting force applied to said surgical device mechanism through said first connector;
    a second mechanical manipulation mechanism configured for receiving motion inputs in a plurality of degrees of freedom and translating said motion inputs into a second set of control signals for controlling motion of said surgical instrument, said second mechanical manipulation mechanism comprising a mechanical manipulator and a control cylinder, said mechanical manipulator of said second mechanical manipulation mechanism comprising:
    a user moveable bi-directional trigger configured for receiving a motion input of said motion inputs;
    a finger loop disposed within said trigger and configured for facilitating a user input of squeezing said trigger in a first direction; and a flange coupled to said trigger and configured for facilitating a user input of pushing said trigger in a second direction, said second direction being opposite of said first direction;

a second mechanical slave cylinder coupled between said control cylinder and said surgical instrument said mechanical slave cylinder configured for moving said surgical instrument in response to said first set of control signals; and a second connector operatively coupled with a control mechanism and said second mechanical slave cylinder, wherein said control cylinder is configured for causing said second mechanical slave cylinder to move said instrument by transmitting force applied to said control mechanism through said second connector wherein said first connector and said second connector comprise a hydraulic system and said hydraulic system comprises a closed-loop hydraulic system; and a plurality of drape interface mechanisms coupled with said surgical device, said plurality of drape interface mechanisms comprising:

at least one drape/handle interface mechanism comprising a first ring defining a first opening through a sterile drape, wherein said sterile drape isolates a portion of a surgical device within a sterile environment, said at least one drape/handle interface mechanism configured for coupling with a control mechanism of said surgical device; and at least one drape/shaft interface mechanism comprising a second ring defining a second opening through said sterile drape, said at least one drape/shaft interface mechanism configured for sealingly receiving said shaft there through as said shaft moves with said piston, wherein said piston is configured for responding to a second set of control signals sent by said first mechanical manipulation mechanism by moving between a proximal end and a distal end of said at least one mechanical slave cylinder coupled with said first mechanical manipulation mechanism.

* * * * *